United States Patent
Ganetzky et al.

(10) Patent No.: US 9,568,468 B2
(45) Date of Patent: Feb. 14, 2017

(54) IN VIVO CELLULAR SCREENING METHODS AND COMPOSITIONS FOR MODELING AND TREATING NERVOUS SYSTEM DYSFUNCTION

(71) Applicant: WISCONSIN ALUMNI RESEARCH FOUNDATION, Madison, WI (US)

(72) Inventors: Barry Ganetzky, Madison, WI (US); Daniel L. Miller, Tacoma Park, MD (US); Shannon L. Ballard, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

(21) Appl. No.: 14/212,999

(22) Filed: Mar. 14, 2014

(65) Prior Publication Data

US 2014/0283149 A1    Sep. 18, 2014

Related U.S. Application Data

(60) Provisional application No. 61/788,568, filed on Mar. 15, 2013.

(51) Int. Cl.
*G01N 33/00* (2006.01)
*A01K 67/00* (2006.01)
*G01N 33/50* (2006.01)
*G01N 33/68* (2006.01)

(52) U.S. Cl.
CPC ...... *G01N 33/5058* (2013.01); *G01N 33/5085* (2013.01); *G01N 33/6896* (2013.01); *G01N 2333/43573* (2013.01); *G01N 2800/2821* (2013.01)

(58) Field of Classification Search
CPC ............ G01N 33/6896; G01N 33/5085; G01N 33/5058
USPC ................................. 800/3, 9, 3.9
See application file for complete search history.

(56) References Cited

U.S. PATENT DOCUMENTS 7,556,944 B2    7/2009  Myers et al.

OTHER PUBLICATIONS

McBrayer et al., 2007, Developmental Cell 13:857-871.*
Li et al., 2001, Neurosci. 106:193-200.*
Rewitz et al., 2009, Science 326:1403-1405.*
Channad-Rezaie et al., 2012, PLoS ONE 7:1-8.*
Aberle, Hermann, et al. "Wishful thinking encodes a BMP type II receptor that regulates synaptic growth in *Drosophila*." Neuron 33.4 (2002): 545-558.
Andlauer, Till FM, and Stephan J. Sigrist. "Quantitative analysis of *Drosophila* larval neuromuscular junction morphology." Cold Spring Harbor Protocols Apr. 2012 (2012): pdb-prot068601.
Anson, Donald. Reporter Genes: A Practical Approach, Humana Press (2007) [cover page, preface and index only].
Auld, Vanessa J., et al. "Gliotactin, a novel transmembrane protein on peripheral glia, is required to form the blood-nerve barrier in *Drosophila*." Cell 81.5 (1995): 757-767.
Awasaki, Takeshi, et al. "Essential Role of the Apoptotic Cell Engulfment Genes draper and ced-6 in Programmed Axon Pruning during *Drosophila* Metamorphosis." Neuron 50.6 (2006): 855-867.
Ayaz, Derya, et al. "Axonal injury and regeneration in the adult brain of *Drosophila*." The Journal of Neuroscience 28.23 (2008): 6010-6021.
Bhattacharya, Martha RC, et al. "A model of toxic neuropathy in *Drosophila* reveals a role for MORN4 in promoting axonal degeneration." The Journal of Neuroscience 32.15 (2012): 5054-5061.
Budnik, Vivian, et al. "Regulation of Synapse Structure and Function by the *Drosophila* Tumor Suppressor Gene dlg." Neuron 17.4 (1996): 627-640.
Dahmann, C. *Drosophila*: Methods and Protocols (Methods in Molecular Biology), Humana Press (2008).
Daniels, Richard W., et al. "Increased expression of the *Drosophila* vesicular glutamate transporter leads to excess glutamate release and a compensatory decrease in quantal content" The Journal of neuroscience 24.46 (2004): 10466-10474.
Del Valle Rodríguez, Alberto, Dominic Didiano, and Claude Desplan. "Power tools for gene expression and clonal analysis in *Drosophila*." Nature methods 9.1 (2012): 47-55.
Eaton, Benjamin A., and Graeme W. Davis. "Synapse disassembly." Genes & development 17.17 (2003): 2075-2082.
Freeman, Marc R., et al. "Unwrapping glial biology: Gcm target genes regulating glial development, diversification, and function." Neuron 38.4 (2003): 567-580.
Fuentes-Medel, Yuly, et al. "Glia and muscle sculpt neuromuscular arbors by engulfing destabilized synaptic boutons and shed presynaptic debris." PLoS biology 7.8 (2009): e1000184.
Ghannad-Rezaie, Mostafa, et al. "Microfluidic chips for in vivo imaging of cellular responses to neural injury in *Drosophila* larvae." PloS one 7.1 (2012): e29869.
Gibbens, Ying Y., et al. "Neuroendocrine regulation of *Drosophila* metamorphosis requires TGFβ/Activin signaling." Development 138.13 (2011): 2693-2703.
Graf, Ethan R., et al. "Stathmin is required for stability of the *Drosophila* neuromuscular junction." The Journal of Neuroscience 31.42 (2011): 15026-15034.
Grueber, Wesley B., Lily Y. Jan, and Yuh Nung Jan. "Tiling of the *Drosophila* epidermis by multidendritic sensory neurons." Development 129.12 (2002): 2867-2878.
Guan, Bo, et al. "The *Drosophila* tumor suppressor gene, dlg, is involved in structural plasticity at a glutamatergic synapse." Current Biology 6.6 (1996): 695-706.
Ito, Kei, Joachim Urban, and Gerhard Martin Technau. "Distribution, classification, and development of *Drosophila* glial cells in the late embryonic and early larval ventral nerve cord." Roux's archives of developmental biology 204.5 (1995): 284-307.

(Continued)

*Primary Examiner* — Christopher M Babic
*Assistant Examiner* — Kelaginamane T Hiriyanna
(74) *Attorney, Agent, or Firm* — Quarles & Brady LLP

(57) ABSTRACT

Described herein are methods and composition for identifying agents that modulate nerve regeneration in vivo in extended third instar (ETI) *Drosophila* larvae. The methods include the use of ETI *Drosophila* larvae having a structural or functional disruption in one or more neurons (e.g., motor neurons) to evaluate a nerve regeneration phenotype over an extended developmental time period in the presence or absence of a test agent.

13 Claims, 16 Drawing Sheets

(56) References Cited

OTHER PUBLICATIONS

Jan, L. Y., and Y. N. Jan. "Properties of the larval neuromuscular junction in Drosophila melanogaster." The Journal of Physiology 262.1 (1976): 189-214.
Kato, Kentaro, et al. "The glial regenerative response to central nervous system injury is enabled by pros-notch and pros-NFκB feedback." PLoS biology 9.8 (2011): e1001133.
Kato, Kentaro et al. "Neuronal programmed cell death induces glial cell division in the adult Drosophila brain." Development 1361 (2009): 51-59.
Koizumi, Keita, et al. "RNA interference screen to identify genes required for Drosophila embryonic nervous system development." Proceedings of the National Academy of Sciences 104.13 (2007): 5626-5631.
Lesch, Christine, et al. "A targeted UAS-RNAi screen in Drosophila larvae identifies wound closure genes regulating distinct cellular processes." Genetics 186.3 (2010): 943-957.
Lunn, E. R., et al. "Absence of Wallerian degeneration does not hinder regeneration in peripheral nerve." European Journal of Neuroscience 1.1 (1989): 27-33.
MacDonald, Jennifer M., et al. "The Drosophila Cell Corpse Engulfment Receptor Draper Mediates Glial Clearance of Severed Axons." Neuron 50.6 (2006): 869-881.
Marques, Guillermo, et al. "The Drosophila BMP type II receptor Wishful Thinking regulates neuromuscular synapse morphology and function." Neuron 33.4 (2002): 529-543.
McBrayer, Zofeyah, et al. "Prothoracicotropic hormone regulates developmental timing and body size in Drosophila." Developmental cell 13.6 (2007): 857-871.
McGuire, Sean E., et al. "Spatiotemporal rescue of memory dysfunction in Drosophila." Science 302.5651 (2003): 1765-1768.
McLachlan, E. M., and A. R. Martin. "Non-linear summation of end-plate potentials in the frog and mouse." The Journal of Physiology 311.1 (1981): 307-324.
Miller, Daniel L., Shannon L. Ballard, and Barry Ganetzky. "Analysis of synaptic growth and function in Drosophila with an extended larval stage." The Journal of Neuroscience 32.40 (2012): 13776-13786.
Nicholson, Louise, et al. "Spatial and temporal control of gene expression in Drosophila using the inducible GeneSwitch GAL4 system. I. Screen for larval nervous system drivers." Genetics 178.1 (2008): 215-234.
Pandey, Udai Bhan, and Charles D. Nichols. "Human disease models in Drosophila melanogaster and the role of the fly in therapeutic drug discovery." Pharmacological reviews 63.2 (2011): 411-436.
Perry, V. H., and M. C. Brown. "Role of macrophages in peripheral nerve degeneration and repair." Bioessays 14.6 (1992): 401-406.
Qurashi, Abrar, et al. "Chemical screen reveals small molecules suppressing fragile X premutation rCGG repeat-mediated neurodegeneration in Drosophila." Human molecular genetics (2012): 2068-2075.
Rewitz, Kim F., et al. "The insect neuropeptide PTTH activates receptor tyrosine kinase torso to initiate metamorphosis." Science 326.5958 (2009): 1403-1405.
Sonnenfeld, Margaret J., and J. Roger Jacobs. "Macrophages and glia participate in the removal of apoptotic neurons from the Drosophila embryonic nervous system." Journal of Comparative Neurology 359.4 (1995): 644-652.
Stebbins, Michael J., et al. "Tetracycline-inducible systems for Drosophila." Proceedings of the National Academy of Sciences 98.19 (2001): 10775-10780.
Wan, Hong I., et al. "Highwire Regulates Synaptic Growth in< i> Drosophila</i>." Neuron 26.2 (2000): 313-329.
Warrick, John M., et al. "Expanded Polyglutamine Protein Forms Nuclear Inclusions and Causes Neural Degeneration in Drosophila." Cell 93.6 (1998): 939-949.
Wen, Hsin-Lan, et al. "Decreased stathmin expression ameliorates neuromuscular defects but fails to prolong survival in a mouse model of spinal muscular atrophy." Neurobiology of disease 52 (2013): 94-103.
Wen, Hsin-Lan, et al. "Stathmin, a microtubule-destabilizing protein, is dysregulated in spinal muscular atrophy." Human molecular genetics (2010): 1766-1778.
Xiong, Xin, and Catherine A. Collins. "A conditioning lesion protects axons from degeneration via the Wallenda/DLK Map kinase signaling cascade." The Journal of Neuroscience 32.2 (2012): 610-615.
Xiong, Xin, et al. "Protein turnover of the Wallenda/DLK kinase regulates a retrograde response to axonal injury." The Journal of cell biology 191.1 (2010): 211-223.
Zito, Karen, et al. "Synaptic clustering of Fasciclin II and Shaker: essential targeting sequences and role of Dlg." Neuron 19.5 (1997): 1007-1016.
Zito, Karen, et al. "Watching a synapse grow: noninvasive confocal imaging of synaptic growth in Drosophila." Neuron 22.4 (1999): 719-729.

\* cited by examiner

Fig. 2A
Fig. 2B
Fig. 2C
Fig. 2D
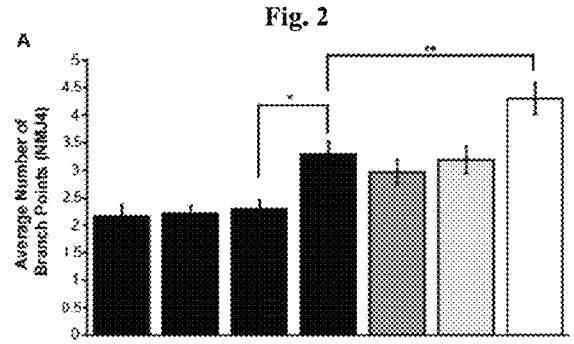
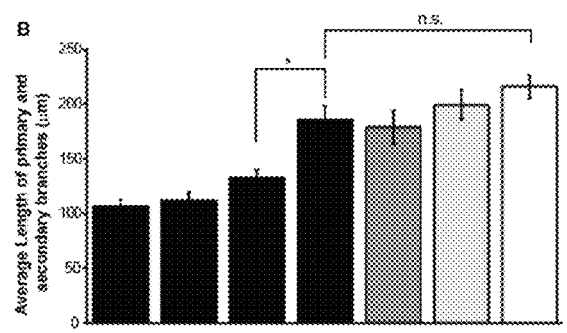
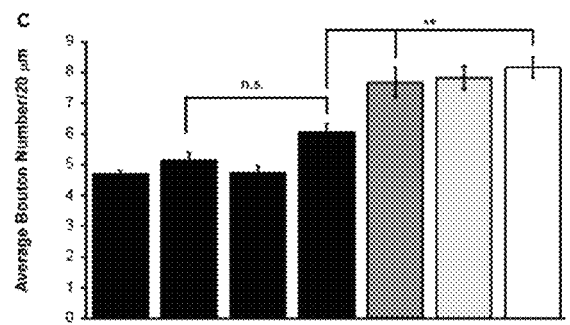
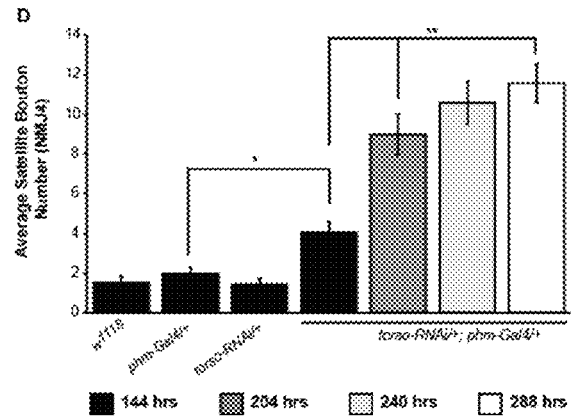
Fig. 2

Fig. 8A
Fig. 8B
Fig. 8C
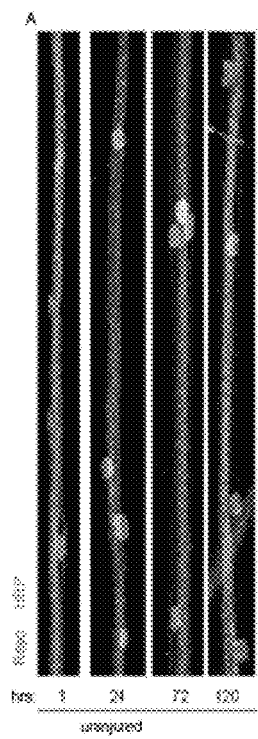
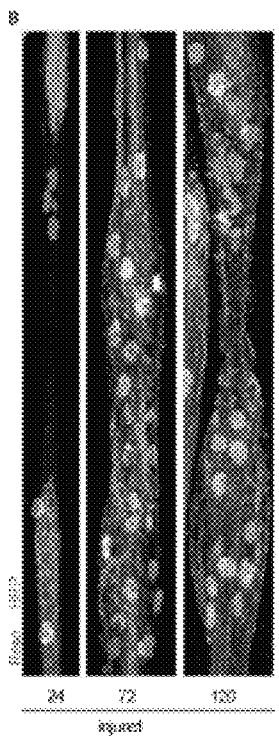
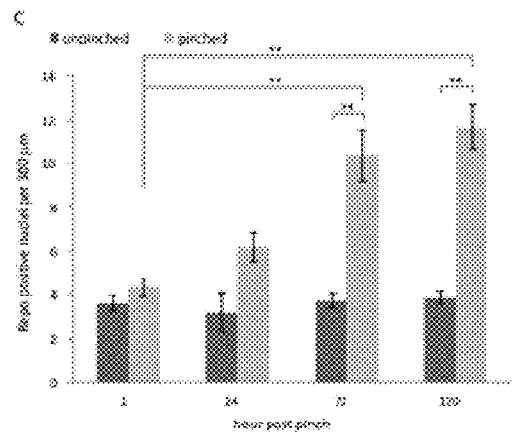

Fig. 9A
Fig. 9B
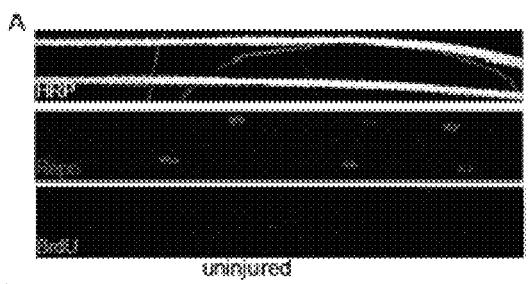
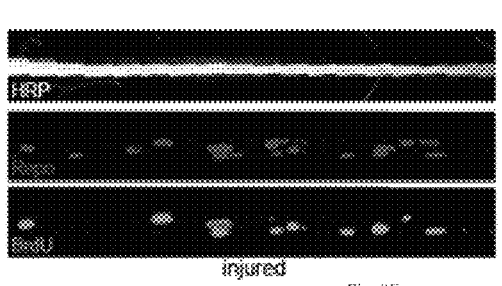
Fig. 9C
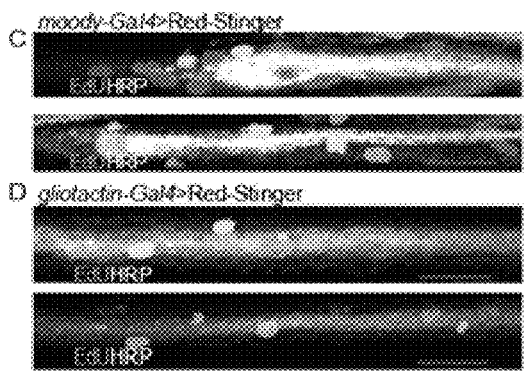
Fig. 9E
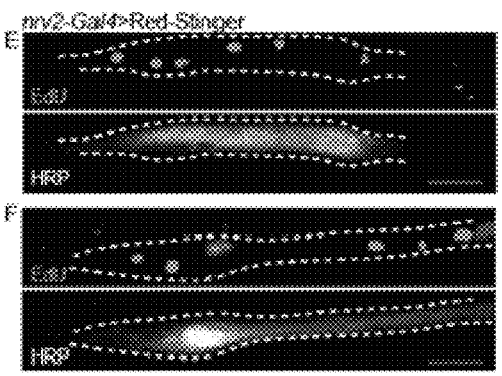
Fig. 9D
Fig. 9F Fig. 12A
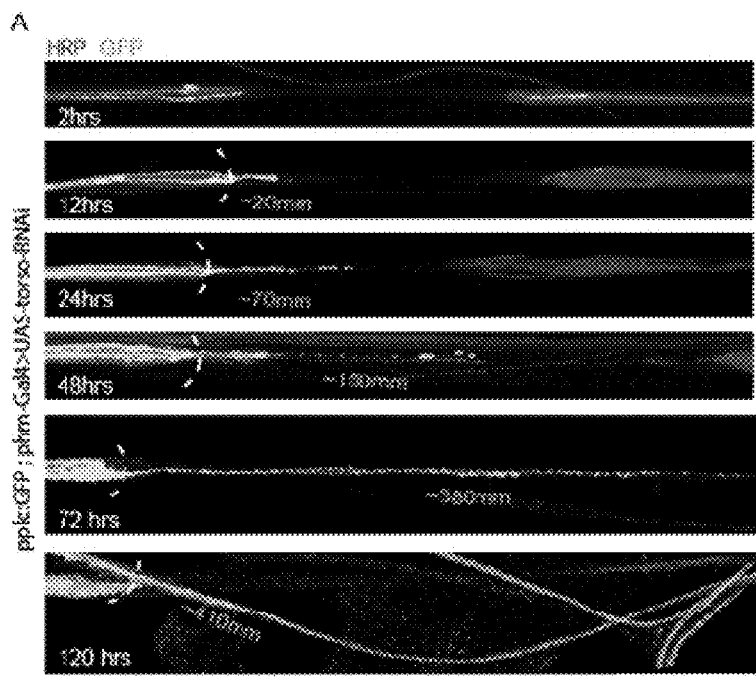
Fig. 12B
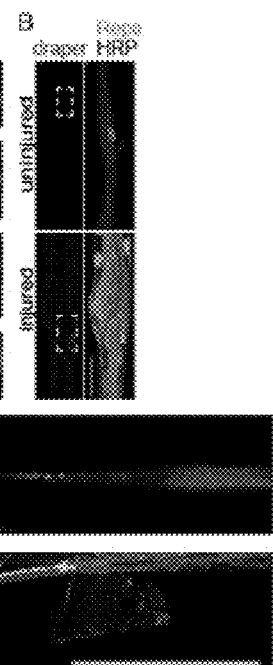
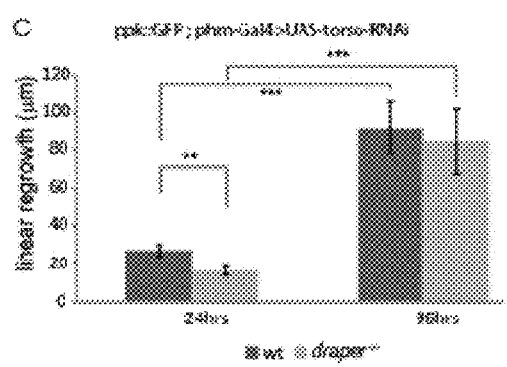
Fig. 12C
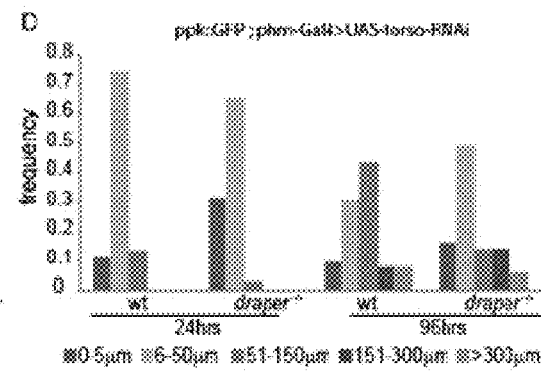
Fig. 12D

IN VIVO CELLULAR SCREENING METHODS AND COMPOSITIONS FOR MODELING AND TREATING NERVOUS SYSTEM DYSFUNCTION

CROSS-REFERENCE TO RELATED APPLICATIONS

This application claims the benefit of U.S. Provisional Patent Application Ser. No. 61/788,568 filed on Mar. 15, 2013.

STATEMENT REGARDING FEDERALLY SPONSORED RESEARCH/DEVELOPMENT

This invention was made with government support under NS015390, NS078342, and NS067843 awarded by the National Institutes of Health. The government has certain rights in the invention.

BACKGROUND

Nervous system conditions ranging from acute injuries such as spinal cord injuries to neurodegenerative diseases such as Alzheimer's disease have been and continue to be among the most intractable health conditions. Thus, there is an ongoing need for disease models and screening systems to identify effective therapies for treating neuronal dysfunction.

The Drosophila larval neuromuscular junction (NMJ) has been a powerful model system for uncovering and characterizing genetic and molecular mechanisms that regulate axonal and synaptic growth, structure, and function. The NMJ offers advantageous features for neurogenetic analyses including a segmentally repeated and stereotypic morphology, which allows easy quantification of morphological and functional properties. In addition, the molecular mechanisms that regulate synapse formation and function are conserved between vertebrates and Drosophila. However, despite these advantages, the short duration of the third instar stage, which lasts only about three days, has limited the use of the larval NMJ as a model system for time-dependent studies. Thus, the larval NMJ is not well-suited for studying biological mechanisms, such as neurodegeneration or nerve regeneration that generally occur over longer time intervals. In principle, this constraint could be overcome if the duration of the larval period could be extended without causing significant perturbations of NMJ structure and function. The mechanisms that maintain NMJ structure over time, how synapses change with age or disease, and long-term effects of neuronal injury could then be investigated in these larvae.

BRIEF SUMMARY OF THE INVENTION

The invention relates generally to methods and compositions relating to the nervous system of a Drosophila larva having a temporally extended third instar stage ("ETI Drosophila larva) for modeling nervous system health conditions and for in vivo screening of candidate agents to treat such conditions.

Accordingly, in a first aspect provided herein is a method for identifying an agent that modulates nerve regeneration in an ETI Drosophila larva, comprising the following steps: (i) contacting with a test agent an ETI Drosophila larva comprising a structural or functional disruption of one or more motor neurons; (ii) assessing one or more of motor neuron axonal growth, neuromuscular junction formation, glial activation, motor neuron survival, or neuromuscular junction loss in the contacted ETI Drosophila larva, and (iii) identifying the test agent as an agent that modulates nerve regeneration if a result of the assessment of step (ii) in the presence of test agent differs from the result of the assessment in the absence of the test agent.

In some embodiments of the first aspect, the ETI Drosophila larva comprises a genetic modification that reduces expression of torso in the prothoracic gland relative to expression of torso in the prothoracic gland of a Drosophila that does not comprise the genetic modification. In some embodiments, where the ETI Drosophila larva comprises a genetic modification to reduce expression of torso, the genetic modification comprises a transgene to express torso RNAi. In some embodiments, torso RNAi is expressed selectively in the prothoracic gland of the ETI Drosophila larva. In one embodiment the genetic modification comprises a phm-Gal4 transgene and a UAS-torso RNAi transgene.

In other embodiments of the first aspect, the ETI Drosophila larva comprises a genetic modification to reduce expression of Smad2 in the prothoracic gland. In some embodiments, the genetic modification comprises aphm-Gal4 transgene and a UAS-Smad2 RNAi transgene.

In further embodiments of the first aspect, the ETI Drosophila larva comprises a phm-Gal4 transgene and a UAS promoter driving expression of an RNAi against dras85D, or dERK.

In some embodiments of the first aspect, the contacting step is performed at least about 144 hours after the egg for the ETI Drosophila larva is laid.

In some embodiments of the first aspect, the ETI Drosophila larva comprises a genetic modification to selectively express a fluorescent reporter in at least one neuron.

In one embodiment, the contacted ETI Drosophila larva comprises a nerve pinch injury to the one or more motor neurons. In other embodiments, the contacted ETI Drosophila larva comprises a genetic modification that induces the structural or functional disruption of the one or more motor neurons. In some embodiments the genetic modification results in expression of at least one heterologous polypeptide associated with a neurodegenerative disease. In some embodiments, the at least one heterologous polypeptide comprises a hAPP, hAbeta$^{1-42}$, a hAtxn3 (Q78) variant, a hTau, a hsynuclein, hhuntingtin, a hTDP-43, a hSOD, hLRRK2, a hGSK3β, or any combination thereof. In some embodiments, where the genetic modification results in expression in expression of the at least one heterologous polypeptide, the genetic modification comprises a lexA expression cassette and a LexA operator-activated expression cassette for expression of the at least one heterologous polypeptide.

In other embodiments of the first aspect, the ETI Drosophila larva comprises a genetic modification to selectively ablate neurons that secrete PTTH by expression of a pro-apoptotic gene (e.g., grim) or a toxin gene (e.g., single chain tetanus toxin).

In a second aspect described herein is a method for inducing genetic modifier mutations of a nerve regeneration phenotype in an ETI Drosophila line, comprising:

(i) performing random mutagenesis on a genetically modified ETI Drosophila line comprising a genetic modification that causes a nerve regeneration phenotype during a larval third instar stage; and (ii) breeding the mutagenized, genetically modified ETI Drosophila line from step (i) to obtain a plurality of randomly mutagenized, genetically modified *Drosophila* lines, wherein the plurality comprises at least one mutagenized, genetically modified *Drosophila* line having a genetic modifier of the nerve regeneration phenotype.

In a third aspect described herein is a method for determining the presence of a mutation that modulates nerve regeneration in an ETI *Drosophila* larva, comprising: (i) providing an ETI *Drosophila* larva that: (a) is generated from a randomly mutated ETI *Drosophila* line; and (b) comprises a structural or functional disruption of one or more motor neurons; (ii) assessing nerve regeneration in an ETI *Drosophila* larva from a randomly mutated ETI *Drosophila* line in the one or more structurally or functionally disrupted motor neurons; and (iii) determining that the randomly mutated *Drosophila* line harbors a mutation that modulates nerve regeneration if nerve regeneration of the one or more motor neurons assessed in the ETI larva from the randomly mutated ETI *Drosophila* line differs from nerve regeneration of one or more structurally or functionally disrupted motor neurons assessed in an ETI *Drosophila* larva from an unmutagenized ETI *Drosophila* line.

In some embodiments of the third aspect, the contacted ETI *Drosophila* larva comprises a nerve pinch injury to the one or more motor neurons.

In some embodiments of the third aspect, the method also includes performing a nerve pinch on a motor neuron of the ETI *Drosophila* larva prior to the assessment in step (i)

In a fourth aspect described herein is a method for identifying a gene that modulates nerve regeneration in an ETI *Drosophila* larva, comprising (i) providing an ETI *Drosophila* larva comprising a structural or functional disruption of one or more motor neurons;

(ii) contacting the ETI *Drosophila* larva, comprising a structural or functional disruption of one or more motor neurons, with: (a) an RNAi to reduce expression of a gene or (b) a nucleic acid that is processed in the ETI *Drosophila* larva to generate RNAi to reduce expression of the gene; (iii) assessing one or more of motor neuron axonal growth, neuromuscular junction formation, glial activation, motor neuron survival, or neuromuscular junction loss in the contacted ETI *Drosophila* larva; and (iv) identifying the gene as a gene that modulates nerve regeneration if nerve regeneration as assessed in the contacted ETI *Drosophila* larva is different from nerve regeneration as assessed in an ETI *Drosophila* larva that is not contacted with the RNAi.

In a fifth aspect described herein is a genetically modified ETI *Drosophila* line, comprising a genetic modification that induces a structural or functional disruption of one or more motor neurons in a third instar larva generated from the genetically modified ETI *Drosophila* line.

In some embodiments of the fifth aspect, the genetic modification comprises expression of at least one heterologous polypeptide associated with a neurodegenerative disease. In other embodiments of the fifth aspect, the genetically modified ETI *Drosophila* line further comprises a genetic modification to selectively express a fluorescent reporter in at least one neuron during the larval third instar stage. In one embodiment the genetic modification to selectively express the fluorescent reporter comprises a ppk::GFP transgene.

In a sixth aspect described herein is a genetically modified ETI *Drosophila* line comprising a genetic modification to selectively express a fluorescent reporter in at least one neuron during the larval third instar stage.

In a seventh aspect provided herein is an in vivo model system for identifying an agent that modulates nerve regeneration, comprising an ETI *Drosophila* larva comprising a structural or functional disruption of its motor nervous system. In some embodiments of the seventh aspect, the ETI *Drosophila* larva further comprises a genetic modification to selectively express a fluorescent reporter in at least one of the one or more motor neurons.

Incorporation by Reference

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

FIG. 8 Peripheral glia proliferate in response to nerve injury. (A) and (B) Peripheral glia nuclei accumulate at nerve injury site. Confocal stacks of peripheral nerves at injury site (B) or at a comparable segment of uninjured nerves (A) at 1, 24, 72, and 120 hrs after injury. Nerves are stained for neuronal membranes (HRP, green) and glial nuclei (Repo, magenta). C. Average number of Repo positive nuclei in peripheral nerves over a 300 μm linear stretch surrounding the injury site (light gray bars), or a comparable 300 μm stretch in uninjured larvae (dark gray bars). All genotypes are phm-Gal4>UAS-torso RNAi. **$p<0.01$.

FIG. 9 Nerve injury induces DNA incorporation in peripheral glia. (A). Anti-BrdU staining of phm-Gal4>torso RNAi larvae fed BrdU for 24 hrs after injury. Incorporation of BrdU in nuclei of peripheral glia in injured larvae (right panels) compared with uninjured larvae (left panels) reveals robust induction of DNA synthesis in response to injury. Confocal images of peripheral nerves stained for HRP (grey), Repo (red) and BrdU (green) 24 hrs after injury. (B-E) Pulse labeling (4 hrs after injury) of larvae reveals acute local EdU incorporation in glial nuclei at injury sites, predominantly in subperinuerial glia (SPGs). Two confocal stacks each of injury stumps from larvae expressing a nuclear Ds-Red either in SPGs (moody-Gal4>Red-Stinger and gliotactin-Gal4>Red-Stinger, panels B. and C. respectively) or wrapping glia, nrv2-Gal4>Red-Stinger (D and E). Dotted lines indicate outline of injury stump. Scale bar: 25 μm.

FIG. 12 draper is required for efficient axonal sprouting of sensory axons following nerve injury (A) ppk::GFP-expressing sensory axons exhibit significant regrowth following axotomy during the extended third larval instar. Confocal stacks showing examples of axonal regrowth in ETI larvae dissected at the indicated times following injury and labeled with antibodies against GFP (green) and HRP (red). Dotted lines indicate the approximate position of the retraction bulb. Anti-GFP antibodies label the regenerating sensory axons, whose linear extension up to and across the injury site increases with time. (B) Draper protein accumulates at injury sites. Panels show stacks of 5 sequential high magnification z-sections of injured and uninjured nerves labeled with antibodies against Draper (red), Repo (green), and HRP (grey) 24 hrs after injury. (C) and (D) loss of draper significantly reduces the efficiency of early sensory axon regrowth after injury. Average linear extension of injured axons at 24 and 96 hrs following injury in draper+ (dark bars) and draper (light bars) ETI larvae (C). Histogram showing the frequency of binned regrowth lengths among all injured axons, in draper+ and draper ETI larvae at 24 and 96 hrs following injury (D). Genotypes in (A), (C), and (D) are either ppk::GFP; phm-Gal4>UAS-torsoRNAi; draper+/draper+ or ppk::GFP; phm-Gal4>UAS-torsoRNAi; draperD5/Df. Genotype in (B) is phm-Gal4>UAS-torso RNAi. $p<0.01$, $*p<0.001$.

Figure 1A:
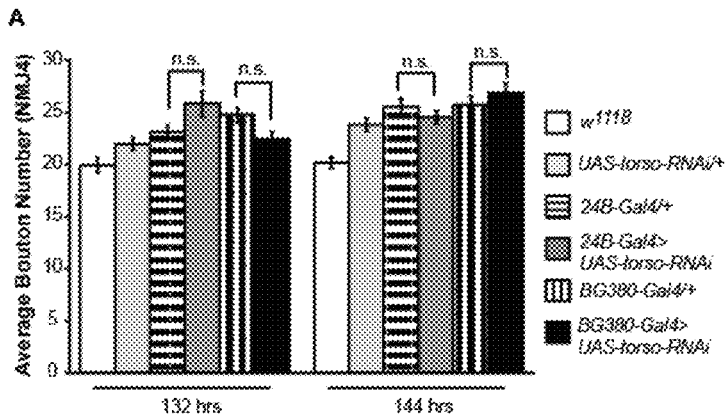
FIG. 1 Synaptic growth is negatively regulated by pre-synaptic ecdysone signaling. (A) Quantification of bouton number at NMJ4 reveals that reduction of torso mRNA levels using RNAi (UAS-torso RNAi) in either the muscle (24B-Gal4) or the motor neuron (BG380-Gal4) does not affect synaptic growth. (B and C) Quantification of bouton number (B) and muscle area (C) at NMJ4 in larvae with reduced ecdysone receptor isoform levels (UAS-EcRA RNAi, UAS-EcRB1 RNAi, or UAS-EcRC RNAi) at 120 hrs AEL. Loss of ecdysone signaling in the motor neuron leads to an increase in bouton number and muscle area compared with control larvae. *$p<0.01$, **$p<0.001$, and n.s.=not statistically significant FIG. 2 Characterization of synaptic morphological features during the extended larval period. (A) Quantification of average branching points at NMJ4. (B) Average length of primary and secondary branches at NMJ4. (C) Average number of boutons per 20 μm along NMJ4 branches. (D) Quantification of average satellite bouton number at NMJ4. phm-Gal4>UAS-torso RNAi larvae exhibit an increase in average branch number, bouton density along the nerve branches, and average satellite bouton number at NMJ4 (A,C,and D). *$p<0.01$, **$p<0.001$, and n.s.=not statistically significant.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

In *Drosophila*, the steroid hormone 20-hydroxyecdysone (20HE) mediates the proper timing of larval molts and metamorphosis. Prothoracicotropic hormone (PTTH), a neuropeptide, stimulates the prothoracic gland (PG) to synthesize and release ecdysone, a precursor of 20HE. A number of studies have shown that experimental manipulations that interfere with the PTTH signaling pathway at any of a number of steps result in a tripling of the third instar larval stage from three days in control larvae to over 9 days, and is referred to as an "extended third instar" because of this greatly extended duration (see, e.g., Rewitz et al, (2009), *Science*, 326:1403-1405). The present invention relates to the inventors' unexpected finding that in ETI *Drosophila* larvae, neuromuscular junction (NMJ) growth continues normally via addition of new branches, satellite boutons, and interstitial boutons. Further, the organization of synapses and active zones remains normal, and synaptic transmission is unchanged. The surprising ability of the *Drosophila* larval neuromuscular system to persist in a normal state over an extended third instar stage, enables for the first time, the use of this in vivo system to model progressive neuronal dysfunction as it occurs, e.g., in neurodegenerative diseases, and also enables screening for genetic and therapeutic candidate modulators of neuronal dysfunction.

I. Definitions

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

In describing the embodiments and claiming the invention, the following terminology will be used in accordance with the definitions set out below.

An "effective amount," as used herein, means an amount of an agent sufficient to evoke a specified cellular effect according to the present invention.

An "extended third instar" or "ETI," as used herein, means a third instar stage that extends beyond about 144 hours after egg laying (AEL) to at least about 600 hours AEL.

An "ETI *Drosophila* larva," as used herein, means a *Drosophila* larva that exhibits an extended third instar stage," as defined herein. For example, the ETI *Drosophila* larva may be derived from an ETI *Drosophila* line. Alternatively, the ETI *Drosophila* larva may be derived from a wild type *Drosophila* line, but subjected to a treatment or condition (e.g., a pharmacological treatment, an antibody treatment, or an RNAi vector treatment) that results in an extended third instar stage.

An "ETI *Drosophila* line," as used herein, means a *Drosophila* line that has been genetically modified such that larvae from the genetically modified line have an extended third instar stage, as defined herein.

"Modulate" or "modulation," as used herein, mean increasing or decreasing a parameter relating to a phenotype of interest, e.g., modulating nerve regeneration.

"Nerve regeneration," as used herein, refers to any process relating to the establishment or loss of structural or functional connectivity of a neuron with its target cell, e.g., a motor neuron forming neuromuscular junctions with target muscle cells; or a first neuron establishing one or more synapses with a second neuron. Examples of such processes include, but are not limited to, axonal elongation, axonal retraction, synaptogenesis, synaptic pruning, neuromuscular junction formation, and post-synaptic receptor clustering.

A "PG-selective promoter," as used herein, refers to a promoter that preferentially, though not necessarily exclusively, drives transgene expression (e.g., GAL4) in the prothoracic gland.

"RNAi," as used herein refers to any of a number of methods or nucleic acid compositions that induce double-stranded RNA/DICER-mediated degradation of a target mRNA in living cells.

A "test agent," as used herein, refers to a molecule assessed for its ability to alter a specific phenotypic endpoint. Examples of test agents include, but are not limited to, (i) organic compounds of molecular weight less than about 600 daltons; (ii) nucleic acids; (iii) peptides (including stapled peptides); (iii) polypeptides; and (iv) antibodies.

II. Methods

Screening Methods

Described herein are methods for identifying an agent that modulates nerve regeneration, where the methods include the following steps: (i) contacting with a test agent an ETI *Drosophila* larva comprising a structural or functional disruption of one or more motor neurons; (ii) assessing one or more of motor neuron axonal growth, neuromuscular junction formation, glial activation, motor neuron survival, or neuromuscular junction loss in the contacted ETI *Drosophila* larva, and (iii) identifying the test agent as an agent that modulates nerve regeneration if a result of the assessment of step (ii) in the presence of test agent differs from the result of the assessment in the absence of the test agent. In other embodiments, the methods include the steps of (i) contacting with a test agent an ETI *Drosophila* larva comprising a structural or functional disruption of one or more sensory neurons; (ii) assessing one or more of sensory neuron axonal growth, sensory neuron synapse formation, glial activation, sensory neuron survival, or sensory neuron synaptic loss in the contacted ETI *Drosophila* larva, and (iii) identifying the test agent as an agent that modulates nerve regeneration if a result of the assessment of step (ii) in the presence of test agent differs from the result of the assessment in the absence of the test agent.

A number of genetic modifications may be used to extend the third instar stage of a *Drosophila* larva, i.e., to generate an ETI *Drosophila* larva or ETI *Drosophila* line. Such genetic modifications inhibit a step in the prothoroacicotropic hormone (PTTH) signaling pathway, the insulin signaling pathway, or both. These signaling pathways modulate the proper timing of larval molts and metamorphosis via control of ecdysone production in the prothoracic gland (PG). Thus, while not wishing to be bound by theory, it is believed that interfering with either of these signaling pathways leads to a reduction of ecdysone in the PG, which results in an extended larval third instar stage. The extended third star larval stage lasts until at least about 150 hours to about 600 hours after egg laying (AEL), e.g., 200 hours, 225 hours, 250 hours, 300 hours, 325 hours, 375 hours, 400 hours, 450 hours, 500 hours, 575 hours, or another period from at least about 200 hours to about 600 hours AEL. In some embodiments, ETI *Drosophila* larvae used in this screening method comprise a genetic modification to reduce the expression of torso, the gene encoding the PTTH receptor, in the PG. Alternatively, the ETI *Drosophila* comprises a genetic modification to reduce expression of another gene critical to regulation of ecdysone synthesis. Such genes include, but are not limited to dSMAD2 ("smox"), dRas, dRaf, and dERK. In some embodiments, expression of such genes, e.g., torso, is reduced by RNAi-mediated knockdown of their corresponding mRNA levels. Typically, where an RNAi approach is to be used, RNAi is expressed endogenously in the ETI *Drosophila* larva via a transgenic expression cassette, for example, where the larva is from an ETI *Drosophila* line. In some embodiments, expression of RNAi targeted to one or more of the aforementioned genes, e.g., torso, is restricted to the PG by the use of a PG-selective promoter to regulate expression of the target RNAi. Typically, the genetically modified *Drosophila* larva will comprise a tissue-selective-transcription factor expression cassette, and a corresponding transcription factor-responsive RNAi cassette. In some embodiments, the genetically modified *Drosophila* larva will comprise a tissue-selective-Gal4 expression cassette, and a Gal4-activated UAS RNAi cassette. In other embodiments, the genetically modified *Drosophila* larva will comprise a tissue-selective LexA expression cassette, and a LexA operator-activated UAS RNAi cassette. The generation and use of such gene expression systems and others is known in the art as described in, e.g., del Valle Rodriguez et al (2012), *Nat Methods*, 9(1):47-55. In some embodiments, the *Drosophila* larva comprises a tissue-selective Gal4 expression cassette, a tissue-selective LexA expression cassette, a Gal4-activated UAS transgene (e.g., an RNAi transgene), and a LexA operator-activated transgene (e.g., a transgene encoding a polypeptided associated with a neurodegenerative disease). In some embodiments, the PG-selective promoter is the phantom promoter. In one embodiment, the ETI *Drosophila* larva to be used comprises a phm-Gal4 transgene and a UAS-torso RNAi transgene. In other embodiments, the ETI *Drosophila* larva comprises a phm-Gal4 transgene and a UAS-Smad2 RNAi transgene. RNAi-based screens in *Drosophila* larvae are well known in the art as described in, e.g., U.S. Pat. No. 7,556,944 and Bhattacharya et al (2012), *J Neurosci*, 32(15):5054-5061, both of which are incorporated by reference herein. Also contemplated herein for use in the methods and compositions described herein are inducible expression systems, which allow temporal and spatial control of transgene expression. For example, in some embodiments, the expression of a ligand or temperature modulated transactivator (e.g., a tetracycline-transactivator "tTA") is driven by a tissue-specific promoter (a PG-selective promoter or a motor neuron-selective promoter) and target transgene is under the control of the ligand-modulated transactivator (e.g., a tet-operator driven transgene). Examples of suitable inducible expression systems include, but are not limited to the, tet-inducible system (Stebbins et al 2001, *Proc Natl Acad Sci USA*, 98(19): 10775-10780), the inducible GeneSwitch GAL4 systems (Nicholson et al 2008, *Genetics*, 178(1):215-234), and the "TARGET" system (McGuire et al 2003, *Science*, 302(5651): 1765-1768).

In other embodiments, the ETI *Drosophila* larva includes a genetic modification to selectively ablate neurons that secrete PTTH by, e.g., expression of a pro-apoptotic gene such as grim. In further embodiments, the ETI *Drosophila* larva includes a genetic modification for expression of a dominant negative variant of a protein in the PTTH signaling pathway, e.g., a dominant negative dras (e.g., dras 85D), draf, or dERK.

Optionally, the ETI *Drosophila* larva may also have a genetic modification for expression of a fluorescent reporter protein (e.g., GFP) in at least one neuron (e.g., a motor neuron). Production of genetically modified *Drosophila* lines and their progeny are established in the art as described in, e.g., Dahmann (2008), *Drosophila: Methods and Protocols* (*Methods in Molecular Biology*), Humana Press.

Examples of suitable fluorescent reporter proteins include, but are not limited to, EGFP and its variants such as YFP, Cyan, and dEGFPs; DS-Red, monomeric Orange and its variants. Other suitable fluorescent proteins are known in the art as described in, e.g., Reporter Genes: A Practical Approach, ed. by Donald Anson, Humana Press (2007). Fluorescent reporter proteins can be imaged and quantified in cells (live or fixed) by a number of known methods in the art, e.g., confocal fluorescence microscopy by direct imaging of reporter-emitted fluorescence or indirectly by immunodetection of the reporter protein in fixed cells. In some embodiments, high content imaging systems (also known as automated microscope systems) can be used for imaging and quantifying fluorescence in live or fixed cells of ETI *Drosophila* larvae to obtain medium- to high-throughput image acquisition. Examples of such instruments include, but are not limited to the Opera (Evotec), ImageXpress (Molecular Devices), and ArrayScan* XTI (Thermo Scientific) instruments. Examples of imaging-based screens (including RNAi screens) in *Drosophila* larvae are known in the art. See, e.g., Koizumi et al (2007), *Proc. Natl Acad Sci USA*, 104(13): 5626-5631; Lesch et al (2010), *Genetics*, 186:943-957; Andlauer et al (2012), *Cold Spring Harbor Protocols*, April (4):481-489, and Ghannad-Rezaie et al (2012), *PLoS One*, 7(1):e29869. doi: 10.1371.

Small molecule compound library, imaging-based screens in *Drosophila* larvae are also known in the art as described in, e.g., Pandey et al (2011), *Pharmacological Rev*, 63(2): 411-436; and Qurashi et al (2012), *Human Mol Genet*, 21(9):2068-2075. Typically compounds are administered to *Drosophila* larvae through formulation in a food substrate. Suitable concentrations of test compounds in food range from about 1 mM to about 10 mM for the purpose of a screen, e.g., about 1.5 mM, 2 mM, 3 mM, 5 mM, 7 mM, 8 mM or another screening concentration from about 1 mM to about 10 mM. Compounds can be administered once, multiple times, or continuously prior to any of the phenotypic assays mentioned herein. Those of ordinary skill in the art will appreciate that the precise timing and dosing of test compound administration will depend on compound stability, compound toxicity and absorption, and the time course of the specific phenotype to be assayed, e.g., rate of axonal elongation, number of neuromuscular junctions formed, glial activation, etc.

Compound libraries for screening are available from a number of commercial sources. Examples of commercial sources for screening libraries include, but are not limited to, Microsource Discovery Systems, Inc. (Gaylordsville, Conn.); ChemBridge Corporation (San Diego, Calif.); and ChemDiv Inc. (San Diego, Calif.).

The test agent contacting step may be performed at least about 150 hours to about 550 hours, e.g., 160 hours, 180 hours, 200 hours, 220 hours, 250 hours, 300 hours, 350 hours, 400 hours, 450 hours, 500 hours, or another period from at least about 150 hours to about 550 hours AEL, i.e., after pupariation would occur in a control (non-ETI) *Drosophila* larva.

In some embodiments of the above-described screening method, the method also includes inducing a structural or functional disruption of one or more neurons in the ETI *Drosophila* larva prior to assessing one of the phenotypic readouts described for step (ii). In some embodiments, the structural or functional disruption is induced in one or more motor neurons.

In some embodiments, the contacted ETI *Drosophila* larva comprises a nerve pinch injury to the one or more motor neurons. Alternatively, the contacted ETI larva comprises a nerve pinch injury to one or more sensory neurons. In other embodiments, the contacted ETI *Drosophila* larva comprises a laser-induced nerve transaction injury. In other embodiments, the contacted ETI *Drosophila* larva comprises a genetic modification that induces the structural or functional disruption of the one or more motor neurons, or one or more sensory neurons. In some embodiments, the genetic modification results in expression of at least one heterologous polypeptide associated with a human neurodegenerative disease or variants thereof that comprise one or more mutations associated with a human neurodegenerative disease, e.g., an expanded polyQ repeat, a non-conservative amino acid substitution. In some embodiments, the at least one heterologous polypeptide comprises a hAPP, hAbeta1-42, a hAtaxin (e.g., Ataxin-3/ATXN3), a hTau, a hSynuclein, hHuntingtin, a hTDP-43, a hSOD, hLRRK2, a hGSK3β, or any combination thereof. Nucleotide sequences for such genes are found in publicly available databases, e.g., GenBank with the following Accession Nos.:hAPP (GenBank 1.NM_000484.3); hATXN3 (NM_001127696.1); hTau (NM_001123066.3), hsynuclein (NM_000345.3), hhuntingtin (NM_002111.6), hTDP-43 (NM_007375.3), hFUS/TLS (NM_004960.3), hSOD1 (NM_000454.4), hGSK3β (NM_002093.3), and hLRRK2 (NM_198578.3), or a protein comprising an expanded polyQ repeat. In one embodiment, the contacted ETI *Drosophila* larva comprises a phm-LexA driver expression cassette, a lexop-smox RNAi expression cassette, a RaFf-Gal4 driver expression cassette, and a UAS-human neurodegenerative polypeptide expression cassette.

In other embodiments, the structural or functional disruption of the one or more motor neurons comprises a chemical insult-induced injury such as by administration of a neurotoxic compound that affects innervation, e.g., taxol as described in Bhattacharya supra.

Also described herein is a method for inducing genetic modifier mutations of a nerve regeneration phenotype in an ETI *Drosophila* line, comprising: (i) performing random mutagenesis on a genetically modified ETI *Drosophila* line comprising a genetic modification that causes a nerve regeneration phenotype during a larval third instar stage; and (ii) breeding the mutagenized, genetically modified ETI *Drosophila* line from step (i) to obtain a plurality of randomly mutagenized, genetically modified *Drosophila* lines, wherein the plurality comprises at least one mutagenized, genetically modified *Drosophila* line having a genetic modifier of the nerve regeneration phenotype.

Also described herein are methods for determining the presence of a mutation that modulates nerve regeneration in an ETI *Drosophila* larva, where the method includes:

(i) providing an ETI *Drosophila* larva that: (a) is generated from a randomly mutated ETI *Drosophila* line; and (b) comprises a structural or functional disruption of one or more motor neurons; (ii) assessing nerve regeneration in an ETI *Drosophila* larva from a randomly mutated ETI *Drosophila* line in the one or more structurally or functionally disrupted motor neurons; and (iii) determining that the randomly mutated *Drosophila* line harbors a mutation that modulates nerve regeneration if nerve regeneration of the one or more motor neurons assessed in the ETI larva from the randomly mutated ETI *Drosophila* line differs from nerve regeneration of one or more structurally or functionally disrupted motor neurons assessed in an ETI *Drosophila* larva from an unmutagenized ETI *Drosophila* line.

Methods for random mutagenesis in *Drosophila* are known in the art, and include, transposon-based mutagenesis (e.g., P-element mutagenesis) and chemical mutagenesis (e.g., with ethane methyl sulfonate).

In some embodiments, assessing nerve regeneration includes one or more of assessing motor neuron axonal growth, neuromuscular junction formation, glial activation, motor neuron survival, or neuromuscular junction loss.

RNAi-based methods may also be used to identify genes that modulate nerve regeneration. Accordingly, also disclosed herein is a method of identifying a gene that modulates nerve regeneration that includes the steps of (i) providing an ETI *Drosophila* larva comprising a structural or functional disruption of one or more motor neurons; (ii) contacting the ETI *Drosophila* larva, comprising a structural or functional disruption of one or motor neurons, with: (a) an RNAi to reduce expression of a gene or (b) a nucleic acid that is processed in the ETI *Drosophila* larva to generate RNAi to reduce expression of the gene; (iii) assessing one or more of motor neuron axonal growth, neuromuscular junction formation, glial activation, motor neuron survival, or neuromuscular junction loss in the contacted ETI *Drosophila* larva; and (iv) identifying the gene as a gene that modulates nerve regeneration if nerve regeneration as assessed in the contacted ETI *Drosophila* larva is different from nerve regeneration as assessed in an ETI *Drosophila* larva that is not contacted with the RNAi.

III. Compositions

Also described herein are compositions and systems that exploit ETI *Drosophila* larvae to analyze progressive changes in the larval nervous system, particularly at neuromuscular junctions under various conditions as described herein.

For example, described herein is an ETI *Drosophila* larva comprising a genetic modification that induces a structural or functional disruption of one or more motor neurons in a third instar stage larva generated from the genetically modified ETI *Drosophila* line. Alternatively, an ETI *Drosophila* larva is provided that comprises a genetic modification that induces a structural or functional disruption of one or more sensory neurons in a third instar stage larva generated from the genetically modified ETI *Drosophila* line.

Examples of a motor neuron structural or functional disruption include, but are not limited to deficits in motor neuron axonal growth, neuromuscular junction formation, and motor neuron survival. Similarly, sensory neuron structural or functional disruption include, but are not limited to, deficits in axonal growth, synaptogenesis, and sensory neuron survival. In some embodiments, the genetic modification that induces a structural or functional disruption of motor neurons in the ETI *Drosophila* larva comprises an expression cassette transgene encoding a polypeptide or polypeptide fragment associated with a neurodegenerative disease. Examples of polypeptides associated with a neurodegenerative disease include, but are not limited to, human orthologs of amyloid precursor protein (APP), Aβ1-42, hAtaxin (e.g., Ataxin-3/ATXN3), Tau protein, Synuclein, TDP-43, superoxide dismutase (SOD)1, glycogen synthase kinase (GSK) 3β, leucine-rich kinase 2 (LRRK2), and combinations thereof. In some embodiments, the genetic modification that induces a structural or functional disruption of motor neurons in the ETI *Drosophila* larva comprises, a loss of function mutation (e.g., due to a P element insertion) in an endogenous *Drosophila* gene associated with neuromuscular junction formation or maintenance (e.g., the Stathmin stai B200 mutation) or a loss of function mutation in a *Drosophila* gene associated with axonal growth. Alternatively, the genetic modification can comprise an expression cassette driving expression an RNAi against the endogenous (wildtype) *Drosophila* gene. In other embodiments, the genetic modification comprises an expression cassette driving expression of a dominant-negative variant of a *Drosophila* gene.

In some embodiments, the above-mentioned genetically modified ETI *Drosophila* line comprises an additional genetic modification for expression of a fluorescent reporter protein (e.g., GFP) in at least one neuron (e.g., a motor neuron). In some embodiments, the genetically modified ETI *Drosophila* line comprises a fluorescent reporter expression cassette under the control of a motor neuron or sensory neuron-selective promoter. In some embodiments, the *Drosophila* line comprises a phm promoter-fluorescent reporter (e.g. GFP) transgene to drive motor-neuron selective reporter expression. In other embodiments, the *Drosophila* line comprises a ppk-driven fluorescent reporter, e.g., GFP to drive sensory neuron-selective fluorescent reporter expression.

Also featured herein is a genetically modified ETI *Drosophila* line, comprising a genetic modification to selectively express a fluorescent reporter, as described herein, in at least one neuron (e.g., a motor neuron or a sensory neuron) during the larval third instar stage.

Also provided herein is an in vivo model system for identifying an agent that modulates nerve regeneration, comprising an ETI *Drosophila* larva comprising a structural or functional disruption of one or more motor neurons, e.g., a nerve pinch injury, or expression of a neurotoxic polypeptide as described herein. In some embodiments, the ETI *Drosophila* larva also includes a genetic modification to selectively express a fluorescent reporter in at least one of the one or more motor neurons.

A feature of an ETI *Drosophila* line is that the extended third star larval stage lasts until at least about 150 hours to about 600 hours after egg laying (AEL), e.g., 200 hours, 225 hours, 250 hours, 300 hours, 325 hours, 375 hours, 400 hours, 450 hours, 500 hours, 575 hours, or another period from at least about 200 hours to about 600 hours AEL.

An ETI *Drosophila* line may be genetically modified to reduce expression of torso in the PG. Alternatively, the ETI *Drosophila* line may comprise a genetic modification to reduce expression of other genes critical to regulation of ecdysone synthesis. Such genes include, but are not limited to dSMAD2, dRas, dRaf, and dERK. In some embodiments, expression of such genes, e.g., torso, is reduced by RNAi-mediated knockdown of their corresponding mRNA levels. In some embodiments, expression of RNAi in the genetically modified *Drosophila* line, targeted to one or more of the aforementioned genes, e.g., torso, is restricted to the PG by the use of a PG-selective promoter to regulate expression of the target RNAi. Typically, an ETI *Drosophila* line will comprise a tissue-selective-Gal4 expression cassette, and a Gal4-activated UAS RNAi cassette. In some embodiments, the PG-selective promoter is the phantom promoter. In one embodiment, the ETI *Drosophila* line comprises a phm-Gal4 transgene and a UAS-torso RNAi transgene. In other embodiments, the ETI *Drosophila* line comprises a phm-Gal4 transgene and a UAS-Smad2 RNAi transgene.

In other cases, an ETI *Drosophila* line comprises a genetic modification to selectively ablate neurons that secrete PTTH by, e.g., expression of a pro-apoptotic gene such as grim or a cell-autonomous cytotoxin. In other cases, the ETI *Drosophila* line comprises a genetic modification to express a dominant negative variant of a protein in the PTTH/Ecdysone pathway, e.g., a dominant negative dras (e.g., dras 85D), raf, or dERK.

The invention will be more fully understood upon consideration of the following non-limiting Examples.

EXAMPLES

Example 1

Materials and Methods

Fly Stocks w1118 was used as a wild-type control for genetic background, and experiments were performed in a w1118 background. phm-Gal4 and UAS-torso RNAi (Rewitz et al, 2009, *Science,* 326:1403-1405) were provided by M. O'Connor (University of Minnesota, Minneapolis, Minn.) and Vienna *Drosophila* RNAi Center (#36280), respectively. hiwND8 (Wan et al., 2000, Neuron, 26:313-329) was provided by A. DiAntonio (Washington University, St. Louis Mo.). BG380-Gal4 was provided by V. Budnik (Budnik et al, 1996, *Neuron,* 17:627-640). The following stocks were obtained from the Bloomington Stock Center: witB11 (Marqueset al., 2002), UAS-EcRA RNAi, UAS-EcRB1 RNAi, UAS-EcRC(97) RNAi, and 24B-Gal4.

Developmental Timing of Larvae

Eggs were laid on apple juice agar plates for 12 hours at 25° C. Newly hatched first instar larvae were collected 36 hours after egg lay (AEL), thus 0-12 hours after hatching. Larvae were placed in softened standard molasses food on apple juice plates and raised at 25° C. Every 36 hours, the larvae were transferred onto fresh molasses food/apple juice plates to avoid desiccation. Larvae were collected at designated time points, placed in $Ca^{2+}$-free saline, and dissected for analysis.

Immunohistochemistry

Female larvae from designated time points were dissected in $Ca^{2+}$-free saline and fixed in 4% paraformaldehyde in PBS for 20 minutes unless otherwise noted. Larval body walls were incubated in primary and secondary antibodies overnight at 4° C. while rocking. They were then mounted in VectaShield (Vector Laboratories) for microscopic analysis. The following antibodies were used: FITC-conjugated anti-HRP at 1:100 (Jackson ImmunoResearch), mouse anti-Dlg at 1:1000 (Developmental Hybridoma Studies Bank), mouse anti-nc82 (Bruchpilot) at 1:250 (Developmental Hybridoma Studies Bank), and anti-DvGlut 1:5000 (generous gift from A. DiAntonio). For use of anti-GluRIII (1:5000) (A. DiAntonio), larvae were fixed in Bouin's fixative for 8 min, followed by antibody incubation as above. Species-specific Alexa-405, Alexa-488, Alexa-568, and Alexa-633 (Invitrogen) secondary antibodies were used at 1:200.

Imaging and Quantification

Quantification of bouton number was performed at NMJ4 due to its relative simplicity. However, comparable phenotypes were observed at other NMJs. Segments A2-A4 were analyzed for bouton number and muscle area. At least 25 NMJs of each genotype were analyzed for each time point. Confocal images were obtained on an LSM 510 confocal microscope (Carl Zeiss, Inc) with Plan-Apochromat 63X NA 1.4 oil differential interference contrast objectives and accompanying software. Images were processed in ImageJ (National Institutes of Health) and Adobe Photoshop software. Muscle area was determined using the draw function of Zeiss AIM software on live DIC images generated on an Axiomager Z1 (Carl Zeiss, Inc). Branch points were defined as any branch of two or more boutons off of the primary nerve terminal and any subsequent branches off of these secondary branches. Branch length was determined using Image J, where arbors of primary and secondary branches nerve terminals were measured starting at the first bouton or branch point after defasciculation (whichever occurred first). For quantification, we defined a bouton as a synaptic swelling compared with neighboring axonal segments that were labeled with the presynaptic marker, α-HRP, and with the postsynaptic marker, α-Dlg. Boutons were quantified directly from immune-stained preparation under a confocal microscope, which afforded better resolution of boutons through the Z plane and enabled visualization of boutons that were not always evident in a photographic image. Satellite boutons were defined as extensions of two or fewer boutons off of the nerve branches. Bouton density was measured by averaging the total number of boutons within the first 20 μm and the terminal 20 μm of primary or secondary branches.

Electrophysiology

Electrophysiology was performed on muscle 6 in segments A3-A5 of larvae at designated time points using standard techniques (Jan and Jan, 1976, *J Physiol,* 262:189-214). Dissections were performed in HL3 saline containing 0.4 mM $Ca^{2+}$, and intracellular recordings were performed in HL3 containing the indicated $Ca^{2+}$ concentration. Recording electrodes (resistance: 15-20 MSΩ) were filled with 3M KCl and stimulating electrodes with saline. Undamaged muscles with a minimum resting potential of 60 mV and input resistance of 5 mΩ, were selected for recording (no significant difference in either parameter was observed across all genotypes and time-points assayed). Recordings were acquired using an AxoClamp 2B amplifier, digitized with an Axon Instruments Digidata 1440A digitizer, amplified with a Brownlee Precision 410 amplifier, and recorded using pClamp10.3 software (Molecular Devices, Sunnyvale, Calif.). Mean EJP amplitudes were calculated from 75 consecutive traces (26-100 of 100 stimulations). Average mEJP amplitude and frequency were determined using Mini Analysis Software v 6.0.7 (Synaptosoft Decatur, Ga.) by averaging 70 consecutive events for each synapse. Quantal content was determined by dividing average EJP amplitude of a synapse by the average mEJP amplitude from the same synapse. For this calculation EJP amplitudes were corrected for non-linear summation according to (McLachlan and Martin, 1981, *J Physiol,* 311:307-324).

Statistical Analyses

Error bars represent SEM, and Student's T-test was performed for all statistical analyses. We report the significance values to be less than 0.01 or 0.001 denoted by one or two stars, respectively.

Example 2

Characterization of NMJ Growth in Larvae with an Extended Third Instar (ETI) Stage Although wild-type larvae typically spend only three days in the third larval instar at 25° C. before undergoing pupariation, this period can be greatly expanded by genetic manipulation of the hormonal mechanism that regulates larval development. The secreted peptide prothoracicotropic hormone (PTTH) triggers production and release of the steroid hormone ecdysone, which regulates progression of larval development. Larvae with reduced transcript levels of the receptor tyrosine kinase torso, the receptor for PTTH (Rewitzet al., supra), in the prothoracic gland (PG) of the ring gland (phm-Gal4>UAS-torso RNAi), remain in the third larval instar for up to nine days. During this ETI stage, larval body size continues to increase. This extension of larval development and enhanced larval growth raises interesting questions about synaptic development. Do larval NMJs stop growing after they reach the maximum size they would achieve during normal larval growth or do they retain sufficient plasticity to continue to grow? If the latter, is NMJ growth coordinated with the increase in muscle size during the extended larval phase? Answers to these questions should reveal important new insights about regulation of NMJ growth not obtainable from studies of wild-type larvae. To address these questions, we examined NMJ morphology of third instar larvae at defined time points after egg lay (AEL), up to the time of pupariation. As one parameter of NMJ growth, we counted the number of boutons per NMJ on muscle 4 (NMJ4). During the third instar, bouton number in w1118 control larvae increased approximately 35% from 84 hrs AEL (14.3±0.5) to pupariation at 144 hrs AEL (19.3±0.7). NMJs of phm-Gal4/+ and UAS-torso RNAi/+ larvae grew from 17.1±0.6 to 24.9±0.8 boutons (46% increase) and 15.7±0.4 to 23.9±1.0 boutons (52% increase), respectively. Previous studies have suggested that this growth is correlated with an increase in the muscle surface area during the same time interval (Guan et al., 1996, *Curr Biol*, 6:695-706). Our data are consistent with this idea. In control larvae, the increase in surface area for muscle 4 parallels the increase in bouton number. From 84 hrs to 144 hrs AEL, muscle area in w1118 larvae increased by 48%, in phm-Gal4/+ larvae by 85%, and in UAS-torso RNAi/+ larvae by 62%. Although the overall rates of growth are greater (see below), we observe a similar parallel increase in phm-Gal4>UAS-torso RNAi larvae, where muscle area and NMJ size increase by 100% and 120%, respectively, between 84-144 hrs AEL. Together, these results support the idea that as larvae progress through the third instar stage, NMJ growth parallels the increase in muscle size.

At early time points of the third instar, NMJ growth in phm-Gal4>UAS-torso RNAi larvae is similar to control larvae. However, at 132 hrs and 144 hrs AEL, phm-Gal4>UAS-torso RNAi larvae display a significant increase in bouton number compared with control larvae (e.g. 24.9±0.8 for phm-Gal4/+ vs. 39.1±1.0 for phm-Gal4>UAS-torso RNAi at 144 hrs AEL). This augmentation of synaptic growth might be explained by a concomitant increase in muscle area. Indeed, phm-Gal4>UAS-torso RNAi larvae exhibit a significant expansion of muscle area at 132 hrs AEL; however, by 144 hrs AEL, phm-Gal4>UAS-torso RNAi larval muscle area does not differ from control larvae. Thus, an increase in muscle area might be associated with the initial addition of boutons at 132 hrs AEL, but it cannot account for the further increase in bouton number at 144 hrs AEL in phm-Gal4>UAS-torso RNAi larvae even before the onset of extended larval development.

Example 3

Presynaptic Ecdysone Signaling Influences NMJ Growth

Figure 1B:
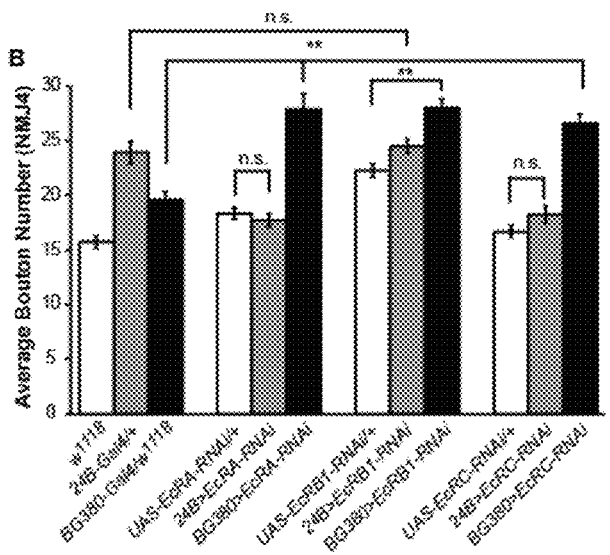
Figure 1C:
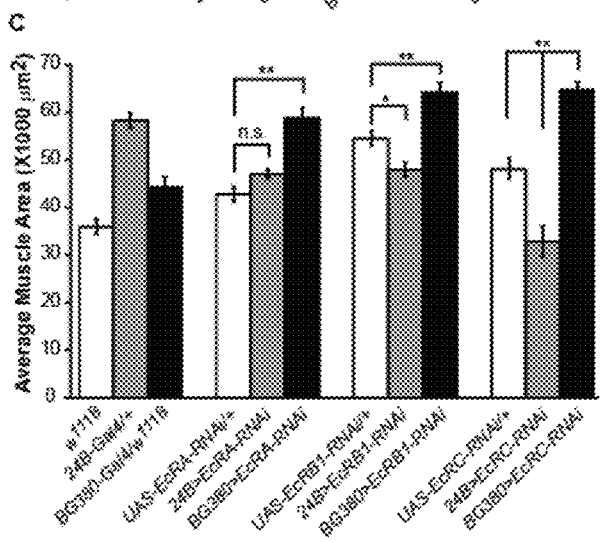

To examine factors other than muscle size that could affect the increase in bouton number at 132 and 144 hrs AEL in phm-Gal4>UAS-torso RNAi larvae, we asked whether a reduction in torso mRNA levels in pre- or post-synaptic cells influences NMJ growth. Although expression of phm-Gal4 has been observed only in the PG, (Rewitz et al., supra), and data not shown), the possibility remains that torso RNAi expression outside the PG could influence NMJ growth. We used the muscle-specific 24B-Gal4 and the neuron-specific BG380-Gal4 drivers to reduce the levels of torso either postsynaptically or presynaptically, respectively. Reduction of torso mRNA in either muscles or neurons does not affect NMJ growth (FIG. 1A). Because the ecdysone precursor is secreted from the ring gland and affects growth and development of distant tissues throughout the entire larva, we tested whether reduction in ecdysone signaling at the NMJ is associated with the observed increase in bouton number at 132 and 144 hrs AEL in phm-Gal4>UAS-torso RNAi larvae compared with controls. There are three characterized isoforms of the ecdysone receptor (EcR): EcRA, EcRB1, and EcRB2. We used BG380-Gal4 and 24B-Gal4 to drive expression of isoform-specific RNAi to reduce levels of EcRA or EcRB1 isoforms either pre- or postsynaptically. We also used an RNAi construct against a common region of all EcR isoforms (UAS-EcRC RNAi) to decrease ecdysone signaling at the NMJ. Reduction of ecdysone receptors postsynaptically does not affect bouton number either at 120 hrs or 132 hrs AEL (FIG. 1B and data not shown). However, presynaptic expression of any of the three EcR RNAi constructs results in a significant increase in bouton number compared with control larvae at 120 hrs AEL (FIG. 1B). This increase in NMJ growth is also observed at 132 hrs AEL in BG380-Gal4>UAS-EcRA RNAi and BG380>UAS-EcRC RNAi larvae (data not shown). The increase in bouton number associated with presynaptic reduction of ecdysone signaling is accompanied by an increase in muscle area (FIG. 1C and data not shown). These results suggest that ecdysone signaling normally functions in motor neurons to restrict NMJ growth and that a reduction in systemic ecdysone titers could promote an early increase in bouton number in phm-Gal4>UAS-torso RNAi larvae even before the onset of extended larval development. Furthermore, the increase in muscle size associated with presynaptic reduction in ecdysone signaling suggests some type of trans-synaptic signaling mechanism by which muscle size also increases as the presynaptic terminal expands.

Example 4

NMJs Continue to Grow During the Extended Third Instar Period

NMJ growth in control larvae terminates with the onset of pupariation around 144 hrs AEL and the subsequent remodeling of the nervous system during metamorphosis. Consequently, one might expect that the mechanisms regulating larval NMJ growth would be selected by evolution to operate only over the normal time interval of the larval stage. However, in phm-Gal4>UAS-torso RNAi larvae, the third larval instar continues for up to six more days beyond the usual onset of pupariation. During this time, the larvae continue to grow, resulting in the production of large pupae (Rewitz et al., supra). Thus, it is of interest to determine whether NMJs in ETI larvae terminate growth after reaching the maximum size for control larvae or if they continue to grow throughout the extended third instar. To investigate this question, we assessed NMJ growth in phm-Gal4>UAS-torso RNAi larvae at various time points up to the onset of pupariation at 288 hrs AEL. Between 144 hrs (onset of pupariation in control larvae) and 288 hrs AEL, the number of boutons continued to increase steadily, reaching 70.8±2.4 boutons, an 80% increase over the bouton count at 144 hrs AEL (39.1±1.0). Until 180-204 hrs AEL, the increase in bouton numbers was paralleled by an increase in muscle growth. However, although NMJ growth continued after 204 hrs AEL, muscle area remained relatively constant thereafter. These results demonstrate that NMJs, as measured by an increase in bouton number, maintain continuous growth throughout the extended third larval instar in phm- Gal4>UAS-torso RNAi larvae indicating that there is no inherent time constraint for NMJ growth nor does NMJ growth terminate upon reaching a certain size. Moreover, only a portion of the overall NMJ growth in phm-Gal4>UAS-torso RNAi larvae occurs in concert with an increase in muscle size. Thus, although NMJ growth and muscle growth usually occur in parallel, they are not necessarily mechanistically coupled and cues other than an increase in muscle size can stimulate NMJ expansion.

To characterize the increase in NMJ growth during the ETI period in phm-Gal4>UAS-torso RNAi larvae in greater detail, we quantified several other morphological parameters in addition to bouton number. One such parameter is the number of branch points per NMJ4. In control larvae, we do not observe any increase in the number of branch points between 84 and 144 hrs AEL (data not shown) consistent with the observations of Zito et al. (1999). At 144 hrs AEL, phm-Gal4>UAS-torso RNAi larvae display a small, but significant increase in branch number compared with control larvae at the same time point (2.3±0.2 for UAS-torso RNAi/+ vs. 3.3±0.2 for phm-Gal4>UAS-torso RNAi) (FIG. 2A) or with phm-Gal4>UAS-torso RNAi larvae at 84 hrs AEL (data not shown). Between 144 and 288 hrs AEL, in phm-Gal4>UAS-torso RNAi larvae the number of branch points per NMJ4 increases further to 4.3±0.3 (FIG. 2A).

We also examined the average length of the NMJ terminal during the ETI by summing the lengths of all primary and secondary branches for each NMJ4 (see Materials and Methods). At 144 hrs AEL, the average terminal length in phm-Gal4>UAS-torso RNAi larvae is larger than in control larvae (133.3±6.7 μm for UAS-torso RNAi/+ vs. 185.9±12.2 μm for phm-Gal4>UAS-torso RNAi) (FIG. 2B). Despite the significant increase in bouton number in phm-Gal4>UAS-torso RNAi larvae between 144 and 288 hrs AEL, the terminal length does not change significantly (185.9±12.2 μm for 144 hrs vs. 215.8±010.5 μm for 288 hrs) (FIG. 2B) resulting in an increase in the relative density of boutons per unit length. We quantified this parameter by determining the average number of boutons within a span of 20 μm along the primary and secondary branches of NMJ 4 (see Materials and Methods). Bouton density at 144 hrs AEL does not differ between control and phm-Gal4>UAS-torso RNAi larvae (FIG. 2C). However, between 144 and 288 hrs AEL, there is a significant increase in bouton density in phm-Gal4>UAS-torso RNAi larvae (6.0±0.3 vs. 8.2±0.4) (FIG. 2C). Finally, we quantified the number of satellite boutons (e.g. small boutons budding off from boutons on the main synaptic axis). In control larvae, there are very few satellite boutons 2/NMJ4) and this number does not increase between 84 and 144 hrs AEL (data not shown). However in phm-Gal4>UAS-torso RNAi larvae, satellite boutons are added steadily throughout the ETI period, reaching a total of at 11.6±1.0 at 288 hrs AEL, a 180% increase compared with 144 hrs AEL (4.1±0.5) (FIG. 2D).

Thus, the increase in bouton number at NMJ4 during the ETI in phm-Gal4>UAS-torso RNAi larvae appears to involve several distinct growth mechanisms. First, there is an increase in the total number of synaptic branches. Second, although these branches do not increase in length they continue to add new boutons interstitially resulting in an increase in bouton density per unit length. Finally, budding of new boutons from pre-existing boutons continues throughout the ETI generating a sizeable increase in the number of satellite boutons.

Example 5

NMJ Growth in phm-Gal4>UAS-torso RNAi Larvae During ETI is Under the Control of Known Growth Regulators Does the continued growth of NMJ4 in phm-Gal4>UAS-torso RNAi larvae during the extended third instar depend on the activities of the same positive and negative regulators of NMJ growth that are known to operate earlier during normal larval development or are entirely new mechanisms engaged? To address this question, we focused on the effects of two key regulatory genes: highwire (hiw), which encodes an E3 ubiquitin ligase that is one of the strongest known negative regulators of NMJ growth (Wanet al., 2000), and wishful thinking (wit), which encodes a type II BMP receptor for the ligand encoded by glass bottom boat (gbb), a potent positive regulator of NMJ growth (Aberleet al., 2002; Marqueset al., 2002). We found that NMJ growth during the ETI period is not only responsive to these regulators, but shows an enhanced sensitivity to their dosage compared to developmentally normal larvae.

We tested the effect of heterozygosity for hiw on NMJ growth in phm-Gal4>UAS-torso RNAi larvae. Between 84 and 144 hrs AEL, phm-Gal4>UAS-torso RNAi larvae heterozygous for hiw (hiwND8/+; phm-Gal4>UAS-torso RNAi) exhibit no significant changes in bouton number at NMJ4 compared with +/+; phm-Gal4>UAS-torso RNAi larvae (39.1±1.0 vs. 36.3±1.3 boutons, respectively). At 156 hrs AEL, 12 hours after control larvae pupariate, hiwND8/+; phm-Gal4>UAS-torso RNAi larvae exhibit a significant increase in bouton number compared with controls (55.9±1.5 vs 37.0±0.8, respectively). This difference in bouton number continues through 264 hrs AEL, indicating that Hiw restricts NMJ growth during the ETI stage as it does during the period of normal larval development. After 240 hr AEL, there is no further NMJ growth in hiwND8/+; phm-Gal4>UAS-torso RNAi larvae and the NMJ growth curves for larvae with one or two copies of wild-type hiw converge at 288 hrs AEL (70.8±2.4 and 69.7±2.8, respectively). The basis of this convergence is unknown but could indicate that an upper limit for the maximum possible number of boutons is eventually reached or that Hiw ceases to have an important role in regulating NMJ growth around this time.

We also examined the role of with during the ETI stage in phm-Gal4>UAS-torso RNAi larvae. Between 84 and 144 hrs AEL, NMJs in phm-Gal4>UAS-torso RNAi larvae with one vs. two copies of wild-type with do not differ in bouton number. However, beginning at 156 hrs AEL, bouton number is reduced in phm-Gal4>UAS-torso RNAi larvae heterozygous for with (26.2±1.0 vs. 33.1±0.9) and this decrease in bouton number persists through 288 hrs AEL (40.1±1.8 vs. 64.2±2.6). Thus, BMP signaling continues to act as an important positive regulator of NMJ growth throughout the ETI period as it does during normal larval development.

Taken together, the results for hiw and with suggest that continued growth during the ETI stage in phm-Gal4>UAS-torso RNAi larvae remains under the control of these two major regulatory pathways as it is during the normal period of larval development, and this is likely to be true also for other NMJ regulatory pathways not examined here.

Example 6

Synaptic Structure is Maintained Throughout the ETI Stage

Larval development in phm-Gal4>UAS-torso RNAi individuals lasts about twice as long as normal, effectively doubling the larval "lifespan." Although this situation offers potentially novel opportunities to investigate time-dependent mechanisms of aging and neuroprotection using the larval NMJ, it is important to determine whether synaptic integrity is maintained in these larvae for the duration of the ETI period. Because the protective mechanisms that normally act to ensure maintenance of synaptic structure and function would likely have evolved to operate over the length of normal larval life, it is possible that as the NMJ ages well beyond its normal duration, NMJ integrity could degrade with time, resulting in disorganization of synaptic proteins and/or disassembly of individual boutons at late time points.

We examined synaptic integrity throughout the ETI period by labeling NMJs of phm-Gal4>UAS-torso RNAi larvae with antibodies to key proteins. Anti-Dlg (Discs large) antibodies were used to label postsynaptic structures (Zito et al, 1997, Neuron, 19:1007-1016) and anti-DvGlut (vesicular glutamate transporter (Daniels et al., 2004, J Neurosci, 24:10466-10474) antibodies were used to label presynaptic structures. Retraction or disassembly of NMJ structures would be expected to manifest as the appearance of synaptic footprints (Eaton and Davis, 2003, Genes Dev, 17:2075-2082), with the loss of postsynaptic proteins, or the accumulation of presynaptic debris (Fuentes-Medel et al., 2009, PLoS Biol, 7:e1000184). Throughout the entire ETI period up to 288 hrs AEL, the association of presynaptic DvGlut and postsynaptic Dlg remained unaltered in phm-Gal4>UAS-torso RNAi larvae as in control larvae and phm-Gal4>torso RNAi larvae at 144 hrs. Despite careful examination of numerous NMJs, we found no evidence for the appearance of ghost bouton structures or post-synaptic footprints. Similarly, examination of synaptic microtubule organization (MT) using antibodies to the MT-associated protein Futsch (22C10), revealed no alterations in the MT cytoskeleton of phm-Gal4>UAS-torso RNAi larvae at 288 hrs compared with control or phm-Gal4>UAS-torso RNAi larvae at 144 hrs AEL controls (data not shown).

To assess formation and maintenance of properly apposed active zones and postsynaptic receptors, we labeled NMJs with antibodies to the common type III glutamate receptor subunit, GluRIII, and the essential active zone protein Bruchpilot, Brp. At 288 hrs AEL, boutons in phm-Gal4>UAS-torso RNAi larvae appear larger and contain more active zones per bouton than normal. However, close apposition of glutamate release sites and receptor fields is maintained. The appearance of unaltered pre- and postsynaptic apposition is not a result of projecting multiple optical slices, since a single 0.5 µm section reveals proper apposition of Brp and GluRIII. For active zones in the single-slice images that appear labeled by Brp antibody only, the corresponding postsynaptic GluRIII clustering is easily identified in adjoining optical slices. These results suggest that the overall appearance and organization of presynaptic and postsynaptic structures is maintained in phm-Gal4>UAS-torso RNAi larvae throughout their expanded larval life.

Example 7

Synaptic Function is Unaffected During the ETI Stage

Figure 3:
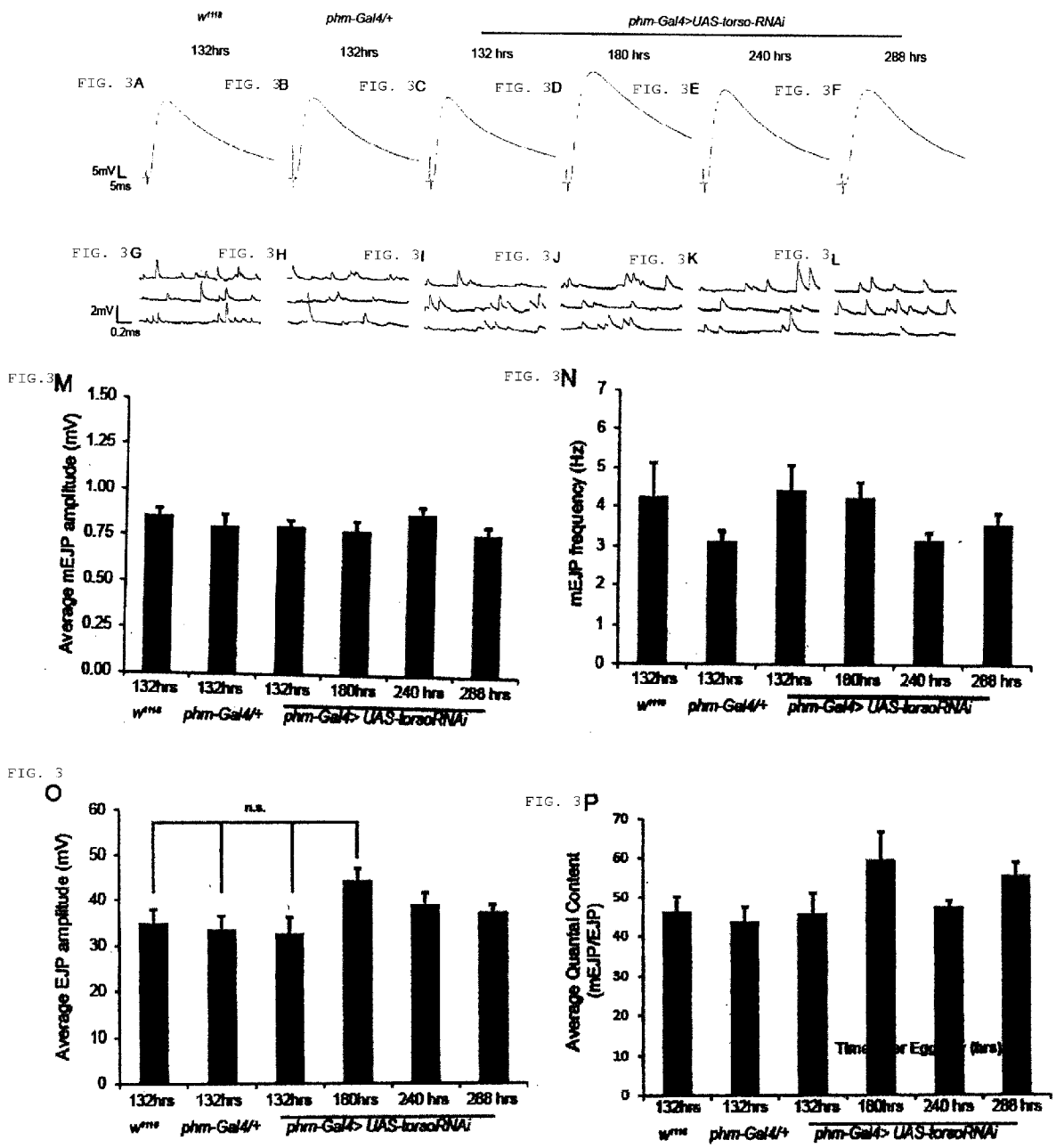
FIG. 3 Larval NMJs remain functionally normal throughout the ETI stage. (A-F) Representative traces of EJPs from third instar larvae of the indicated genotypes and time points after egg lay. (G-L) Representative traces of spontaneous neurotransmitter release (mEJPs) of from third instar larvae of the indicated genotypes and time points after egg lay. All recordings (A-L) were acquired in 1.0 mM Ca2+. (M-P) Quantification of average mEJP amplitude (M), average mEJP frequency (N), average EJP amplitude (O), and average quantal content (P).

Despite the normal appearance of presynaptic and postsynaptic structures at NMJs in phm-Gal4>UAS torso RNAi larvae, more subtle perturbations could accumulate over time resulting in defects in synaptic function. To examine this possibility, we monitored NMJ function over time by recording both spontaneous and evoked transmitter release in phm-Gal4>UAS torso RNAi larvae (FIG. 3) throughout the ETI period. At 132 hrs AEL, we find no difference in phm-Gal4>UAS torso RNAi larvae compared with controls in amplitude of excitatory junctional potentials (EJPs) (FIGS. 3A-F and O), amplitude of spontaneous miniature EJPs (mEJPs) (FIGS. 3G-L,and M), frequency of mEJPs (FIGS. 3G-L and N), or in quantal content (FIG. 3P). Moreover, these parameters do not change significantly over time in phm-Gal4>U AS torso RNAi larvae for the entire duration of the ETI period (FIG. 3). These data strongly suggest that NMJ function, like NMJ structure, remains essentially normal in phm-Gal4>UAS torso RNAi larvae despite the fact that these synapses persist twice as long as in control larvae.

Example 8

An ETI Model of Synaptic Degeneration Based on Expression of Human CAG Expanded Triplet Repeat Ataxin-3 (ATXN3)

We sought to test whether human gene mutations that cause neurodegeneration cause synaptic degeneration at the larval NMJ in an ETI background where the third instar is sufficiently long to allow permit synaptic pathology to develop.

Methods

Spinocerebellar ataxia type 3, also known as Machado-Joseph Disease (MJD), is an autosomal dominant neurodegenerative disorder in humans that causes progressive cerebellar ataxia. It is the most common dominantly inherited ataxia in humans. The disease is caused by mutations in the ataxin-3 (ATXN3) gene resulting in an expansion of CAG repeats (triplet repeats) generating a mutant protein containing a segment with an expanded number of consecutive glutamine residues (polyglutamine repeat; normal number of repeats is 13-41). Expression of the abnormal protein with an expanded polyglutamine repeat (e.g. 78 residues) results in death of neurons in the hindbrain. MJD has been modeled in adult Drosophila by expressing a truncated version of the human ATXN3 gene containing 78 triplet repeats (ATXN3: Q78) (Warrick et al., 1998, Cell, 93:939-949). Expression of the mutant protein in the eye results in a loss of photoreceptor neurons, whereas expression of a gene encoding a protein with a normal number of repeats (ATXN3:Q27) has no deleterious effect.

The size and accessibility of the larval NMJ make it possible to characterize and investigate defects in synaptic degeneration at much higher resolution than for synapses in the central nervous system. Thus, we were interested in determining whether expression of the same ATXN:Q78 transgene used by Warrick et al. (1998) in the larval nervous system would cause defects in NMJ structure or stability. As the disease phenotype in humans is progressive and age-dependent, we performed the experiment in an ETI background to allow a sufficient length of time at the third larval instar for any deleterious effects to become manifest.

We expressed smox RNAi in the prothoracic gland. smox encodes the Smad2 protein, a transcriptional co-activator of two different pathways required for ecdysone synthesis. By knocking down smox expression in the prothoracic gland, there is an even stronger reduction in ecdysone synthesis than knocking down torso expression. Knock down of smox delays pupariation to over 600 hours after egg lay (e.g. an expansion of the third instar to over 20 days after egg lay). The LexA/LexAop expression system was used to drive expression of smox in the prothoracic gland. By doing so, we were able to use the Gal4/UAS system in the same larvae to drive expression of ATXN3 in motor neurons. We thus contructed phm-LexA to express the LexA transcriptional regulator in the prothoracic gland and LexAop-smox RNAi to transcribe smox RNAi in response to the LexA protein. Finally, we used the RRaF-Gal4 driver (provided by Miki Fujioka, Thomas Jefferson University) to express UAS-ATXN:Q78 (or UAS-ATXN:Q27 as control) specifically in larval motor neuron 1 (MN1, which forms NMJ1 on the corresponding body wall muscle).

The experimental larvae (LexAop-smox RNAi; UAS-ATXN3:Q78; RRaF-Gal4/phm-LexA) were constructed by appropriate crosses and examined at various time points after egg lay for the appearance and integrity of NMJ1. Since ATXN3:Q78 was expressed specifically in MN1, we examined NMJ4 in the same segment in the same larvae as an internal control. We performed the same analysis in LexAop-smox RNAi; phm-LexA; RRaF-Gal4/UAS-ATXN3:Q27 larvae to compare the effects of expressing a mutant ataxin 3 protein containing an expanded polyglutamine repeat versus an ataxin 3 with a normal repeat number.

Experimental and control preparations were dissected in the same dish in *Drosophila* saline (128 mM NaCl, 2 mM KCl, 4 mM $MgCl_2$, 0.1 mM $CaCl_2$, 35.5 mM sucrose, 5 mM HEPES). Preps were fixed in Bouin's fixative for 5 min and then rinsed for 30-90 minutes in multiple changes of PBS with 0.1% triton (PBST). Preps were incubated in primary antibody at 4° C. for 1-3 days. Primary antibodies were: Alexa Fluor 647 goat anti-horseradish peroxidase at 1:1000 (Jackson ImmunoResearch Laboratories), anti-nc82 at 1:250 (Developmental Studies Hybridoma Bank), anti-GluRIIa at 1:50 (Developmental Studies Hybridoma Bank). All antibodies were diluted in PBST with 2% normal goat serum (NGS). Preps were rinsed at room temperature over multiple hours in multiple changes of PBST, and then incubated in secondary antibody for 1-2 hours. Secondary antibodies were: Alexa Fluor 568, goat anti-mouse IgG1 (γ1) (Invitrogen) and Alexa Fluor 488 goat anti-mouse IgG2a (γ2a) (Invitrogen). Secondary antibodies were diluted at 1:200 in PBST-NGS. After removing the secondary antibody, preps were rinsed again for 1-3 hours in multiple changes of PBST and then mounted onto slides in Vectashield mounting medium for imaging. NMJs were stained with anti-horseradish peroxidase (blue), which stains axonal membranes; anti-bruchpilot (red), a marker for presynaptic active zones; and anti-glutamate receptor III (green), a marker for post-synaptic active zones.

Slides were imaged using a Zeis LSM 510 confocal microscope with an alpha plan-apochromat 100×/1.46 objective, and 633 nm, 561 nm and 488 nm wavelength lasers. The pinholes were 1.01 Airy Units (AU) for 633 nm, 0.88 AU for 561 nm and 0.99 AU for 488 nm. Pixel dwell time was 3.20 μs. The step size was 0.4 μm, and the pixel size was 0.082 μm×0.082 μm. The amplifier offset and detector gain was optimized for maximum range detection for every NMJ4 on each preparation. The optimized NMJ4 setting for each segment was used to image NMJ1 of the same segment. Projections were made using pixel maximums.

Results

Figure 4:
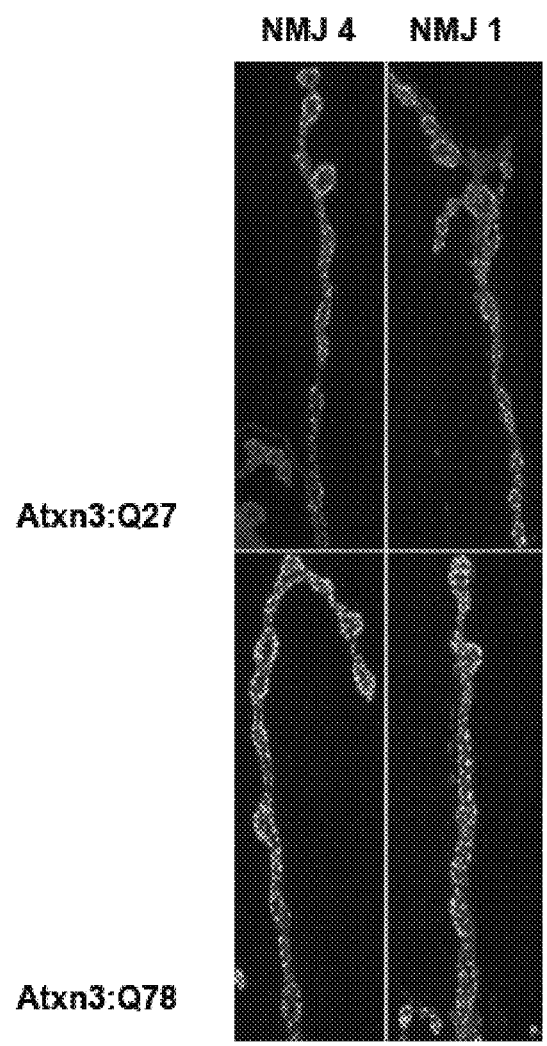
FIG. 4 Synaptic morphology is normal in ETI larvae expressing Atxn3 containing an expanded triplet repeat 10 days after egg lay. Truncated human Atxn3 gene containing a normal polyglutamine repeat of 27 glutamines (Atxn3:Q27) (top left and right panels) or an expanded repeat of 78 glutamines (Atxn3:Q78) (bottom left and right panels) was driven under the control of RRaF-Gal4, which is expressed specifically in motor neuron 1. Images of NMJ4 (left top and bottom panels) from the same larvae and same larval segment as the images of NMJ1 (right top and bottom panels) serve as internal controls because the Atxn3 transgenes are not expressed in motor neuron 4. Note that overall staining pattern and synaptic morphology is indistinguishable between NMJ4 and NMJ1 regardless of whether motor neuron 1 is expressing Atxn3:Q27 or Atxn3:Q78. Staining pattern and morphology for NMJ1 is indistinguishable in both cases as well. Age of larvae in all panels is 10 days after egg lay. NMJs are stained with anti-horseradish peroxidase (blue), which stains axonal membranes; anti-bruchpilot (red), a marker for presynaptic active zones; and anti-glutamate receptor III (green), a marker for postsynaptic active zones.
Figure 5:
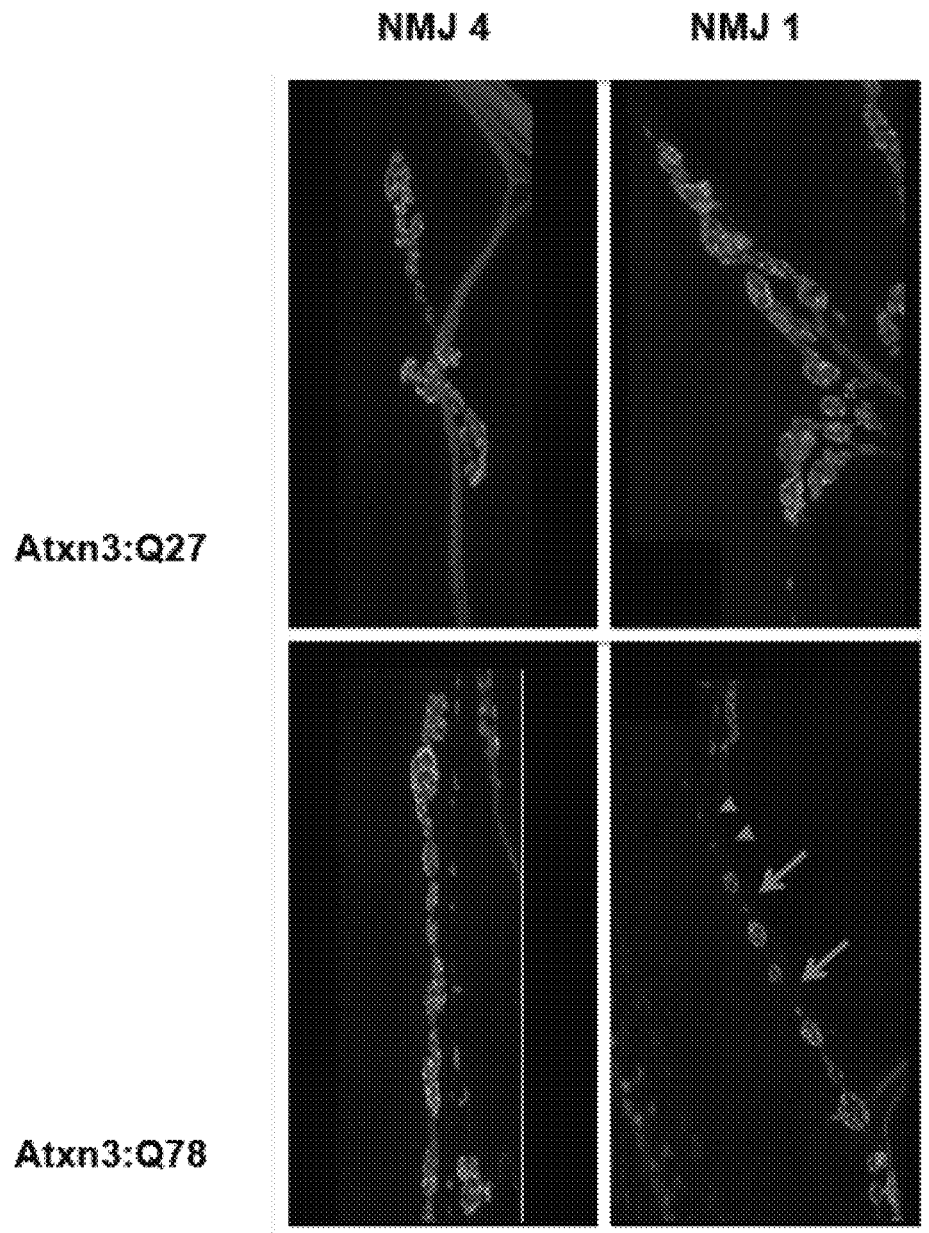
FIG. 5 Synaptic degeneration in ETI larvae expressing Atxn3 containing an expanded triplet repeat. Truncated human Atxn3 gene containing a normal polyglutamine repeat of 27 glutamines (Atxn3:Q27) (top left and right panels) or an expanded repeat of 78 glutamines (Atxn3:Q78) (bottom left and right panels) was driven under the control of RRaF-Gal4, which is expressed specifically in motor neuron 1. Images of NMJ4 (left top and bottom panels) from the same larvae and same larval segment as the images of NMJ1 (right top and bottom panels) serve as internal controls because the transgenes are not expressed in motor neuron 4. Note that NMJ1 in larvae expressing Atxn:Q78 show structural discontinuity of the motor axon connecting adjacent boutons (arrows) as well as decaying boutons (arrowheads). Age of larvae in all panels is 24 hours after egg lay. NMJs are stained with anti-horseradish peroxidase (blue), which stains axonal membranes; anti-bruchpilot (red), a marker for presynaptic active zones; and anti-glutamate receptor III (green), a marker for postsynaptic active zones.
Figure 6:
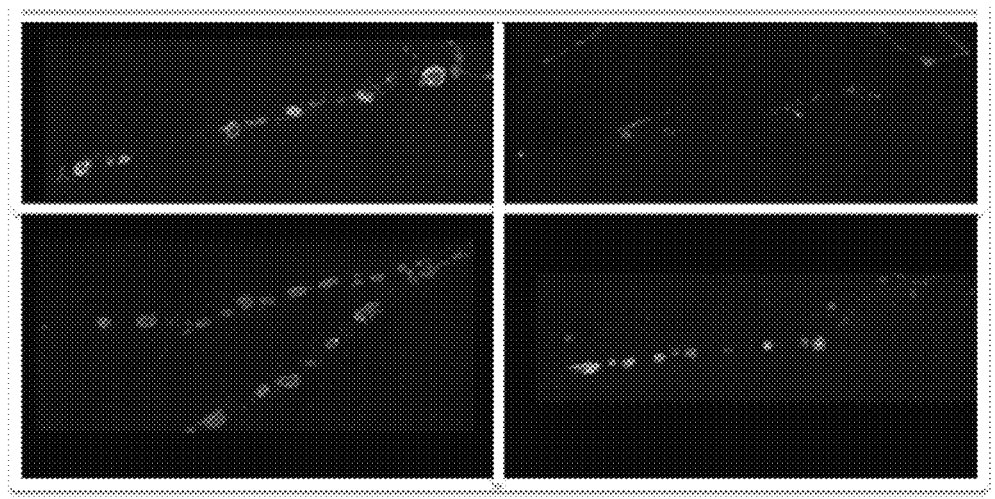
FIG. 6 Synaptic degeneration in ETI larvae expressing Atxn3 containing an expanded triplet repeat. Truncated human Atxn3 gene containing a normal polyglutamine repeat of 27 glutamines (Atxn3:Q27) (top panels) or an expanded repeat of 78 glutamines (Atxn3:Q78) (bottom left and right panels) was driven under the control of RRaF-Gal4, which is expressed specifically in motor neuron 1. Images of NMJ4 (left top and bottom panels) from the same larvae and same larval segment as the images of NMJ1 (right top and bottom panels) serve as internal controls because the transgenes are not expressed in motor neuron 4. Note that NMJ1 in larvae expressing Atxn:Q78 show structural discontinuity of the motor axon connecting adjacent boutons (arrows) as well as decaying boutons (arrowheads). Age of larvae in all panels is 24 hours after egg lay. NMJs are stained with anti-horseradish peroxidase (blue), which stains axonal membranes; anti-bruchpilot (red), a marker for presynaptic active zones; and anti-glutamate receptor III (green), a marker for postsynaptic active zones.

We examined experimental and control NMJs by confocal microscopy after immunostaining NMJs with various antibodies for pre- and post-synaptic markers. The overall size and morphology of NMJ1 in larvae expressing ATXN:Q78 was normal (as compared with NMJ4 in the same segment in the same larvae and as compared with larvae expressing ATXN:Q27) in larvae at 10 days (FIG. 4) and up to 15 days after egg lay. However, at 25 days after egg lay we observed substantial synaptic degeneration specifically in NMJ1 in larvae expressing ATXN:Q78 but not ATXN:Q27 (FIG. 5). This degeneration was apparent as disruption of the structural continuity of NMJs, bouton decay and loss, and disappearance of presynaptic and postsynaptic components of synaptic structure (FIGS. 5 and 6). We observed these defects in structural integrity in 32% of NMJs in the experimental larvae, whereas only 2% of NMJs in control larvae exhibit any defects.

Example 9

The Time Course of Presynaptic and Postsynaptic NMJ Disassembly Following Nerve Injury Previous studies of nerve injury and regeneration in *Drosophila* larvae have been temporally limited by the onset of metamorphosis. We recently characterized a novel long-lived larval experimental system that expands the duration of the larval third instar from 2.5 to nearly ten days while retaining normal function and developmental properties of the nervous system (Miller et al., 2012). As an important step in establishing ETI larvae as a valid model to study time-dependent neurological processes, the ETI background was utilized in combination with an established larval nerve injury crush assay (Xiong et al., 2010; Xiong and Collins, 2012), to probe synaptic degeneration and clearance and axonal regrowth over a time-frame previously not accessible in normal larvae.

Methods

Fly Stocks w1118 was used as a wild-type control for genetic background, and experiments were performed in a w1118 background. The phm-Gal4 and UAS-torso RNAi line is described in (1). The draperΔ5 (null allele of draper) line is described in (4). The following stocks were obtained from the Bloomington Stock Center: moody-Gal4, gliotactin-Gal4, nrv2-Gal4, ppk:eGFP, Df(3L)BSC181 (draper deficiency, stock number 9693).

Immunohistochemistry and Developmental Timing of Larvae

Dissections and Immunohistochemistry was performed as previously described (3). Rb-anti-GFP (Life technologies A-11122) was used at 1:1000, ms-anti-Repo (Developmental Hybridoma Studies Bank) was used at 1:50, and Rb-anti-Draper (4) (provided by Mark Freeman, UMass Medical School) was used at 1:500. EdU staining was done as recommended by the manufacturer (Click-iT® EdU Alexa Fluor® 488 Imaging Kit, C10337); briefly, larvae were dissected in warm PBS, then incubated at 37 C in M3 complete medium with 100 μM Edu for 2 hrs, washed twice with PBS, fixed, and then processes as usual for antibody staining Imaging and Quantification Imaging was performed as described previously(3). Glial nuclei count was done using AIM software while live scanning on a Zeiss LSM 510. The scan was focused on the injury site. A 300 μm linear segment was measured that spanned one injury stump, terminating at the retraction bulb. All Repo positive nuclei were counted within that segment. Glial nuclei in uninjured peripheral nerves were counted in a 300 μm segment at a comparable location. Axon regeneration was quantified by measuring the linear extension of GFP positive neurites from the retraction bulb into the injury site. Axon extension in the opposite direction, away from the injury site, was not measured.
Statistical Analyses
As Described Previously (3)

References for Methods Section

1. K. F. Rewitz, N. Yamanaka, L. I. Gilbert, M. B. O'Connor, *Science* 326, 1403 (Dec. 4, 2009).
2. T. Awasaki et al., *Neuron* 50, 855 (Jun. 15, 2006).
3. D. L. Miller, S. L. Ballard, B. Ganetzky, *J Neurosci* 32, 13776 (Oct. 3, 2012).
4. M. R. Freeman, J. Delrow, J. Kim, E. Johnson, C. Q. Doe, *Neuron* 38, 567 (May 22, 2003).

Results

Figure 7A:
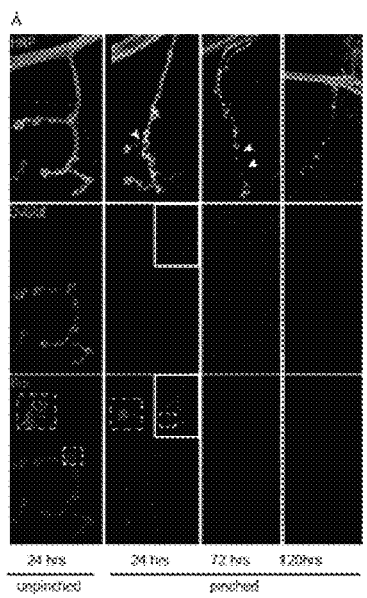
FIG. 7 Kinetics of pre- and postsynaptic NMJ disassembly following motor neuron injury. (A) Rapid disassembly of presynaptic active zones. Confocal stacks showing NMJs of injured (left column) and uninjured (columns 2-4) motor axons at 24, 72, and 120 hrs after injury. Dissected preparations are stained with antibodies for DvGlut (magenta) and Brp (red). Inserts show high intensity scans for DvGlut and Brp (framed by solid white lines) and magnification of single boutons (framed by dashed white lines). (B) Dlg positive postsynaptic densities continue to be maintained at sites containing presynaptic membrane fragments. Confocal stacks showing NMJs of injured (left column) and uninjured (columns 2-4) motor axons at 24, 72, and 120 hrs after injury labeled with antibodies against HRP (green) and Dlg (red). (C) Continued maintenance of postsynaptic receptor clusters at sites opposite remaining presynaptic membrane fragments. Confocal stacks showing NMJs of injured (left column) and uninjured (right two columns) motor axons at 48 and 96 hrs after injury labeled with antibodies for HRP (gray), Brp (green), and Pak (red). All genotypes are phm-Gal4>UAS-torso RNAi. Arrowheads indicate discontinuities in the integrity of NMJs undergoing neurodegeneration. NMJ4 is shown in all images.
Figure 7B:
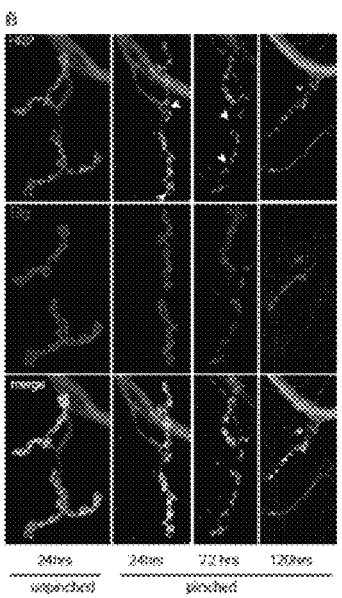

Previous work has established that over the course of 24 hrs following nerve injury, NMJs of injured motor neurons shrink, active zone proteins disappear, and terminals begin to fragment (Xiong et al., 2010; Xiong and Collins, 2012). To determine whether ETI larvae exhibit the same initial responses to injury as standard wild-type larvae, we performed nerve crush on ETI larvae at 120 hrs after egg lay, corresponding to the wandering third instar stage in standard larvae, and examined the subsequent consequences. We found that by 24 hrs after injury there were large accumulations of the vesicular glutamate transporter DvGlut (Daniels et al., 2004), at the anterior injury stump (data not shown), and accumulation of Brp at both the anterior and posterior stumps indicating that both anterograde and retrograde transport were blocked (data not shown). In addition, 24 hrs after nerve crush, DvGlut was completely absent from the NMJs of damaged motor neurons, Brp was significantly reduced, and its distribution was disrupted (FIG. 7A). Further, bouton size was decreased, and arbors were spindly and discontinuous (FIGS. 7A and 7B). These results faithfully recapitulate the features of motor neuron injury in standard larvae, indicating that ETI larvae are appropriate for examining longer term consequences after nerve damage.

Figure 7C:
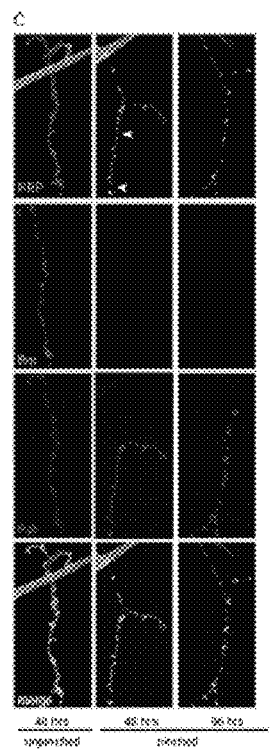

To examine the subsequent time course of synaptic disassembly, we stained NMJs following nerve crush with additional antibodies and characterized pre- and post-synaptic changes for up to 120 hrs after injury. As revealed by HRP staining, fragmentation of the NMJ was evident throughout the terminal by 48hr after injury (FIG. 7C, arrowheads) and by 72 hrs large gaps appeared between the remaining segments of terminal (FIGS. 7A and 7B, arrowheads). Fragmentation and elimination of NMJ material continued progressively through 96 hrs (FIG. 7C) and by 120 hrs much of the presynaptic motor-terminal membrane was eliminated, resulting in a thin, shortened, and completely discontinuous remnant (FIGS. 7A and 7B). In undamaged NMJs, DvGlut and Brp are detectable with equal intensity. However, these two presynaptic proteins differ significantly in the dynamics of their removal following injury. Whereas DvGlut protein becomes undetectable within 24 hrs, Brp remains present in most boutons at 24 hrs and did not fully disappear until 72 hrs after injury (FIGS. 7A and 7C, and data not shown). This result suggests that the two active zone-associated proteins are removed by different mechanisms.

In contrast, disassembly of the postsynaptic machinery after injury followed a different time course. The level and distribution of the postsynaptic scaffolding protein, Disks-large (Dlg) (Zito et al., 1997), exhibited little difference at NMJs of injured vs. uninjured larvae 24 hrs after nerve crush (FIG. 7B). Dlg staining remained relatively intact until about 72 hrs after injury, at which point its distribution mirrors the presynaptic discontinuities. At boutons that still persist at that time, staining for Dlg shows little loss of intensity (FIG. 7B, arrowheads). Postsynaptic Dlg staining continues to parallel presynaptic HRP staining up to 120 hrs after injury. Similarly, staining for PAK, which closely co-localizes with glutamate receptors, remained detectable at full intensity even at 96 hrs after injury in all regions where presynaptic membrane was still intact (FIG. 7C). These results suggest that whereas presynaptic active zones are dismantled rapidly following nerve crush giving rise to fragmenting NMJs devoid of release machinery, postsynaptic densities and receptor fields remain present wherever any remnant of presynaptic membrane continues to contact muscle.

Example 10

Nerve Injury Stimulates Local Glial Proliferation

Following nerve crush, we noticed that glial nuclei, stained with antibodies against the pan-glial marker Repo were present with increased abundance at the injury site by 72 hrs after injury (FIG. 8). As stab injury in the CNS of larvae or adults can induce surrounding glial cells to proliferate(Kato et al., 2009; Kato et al., 2011), we tested whether peripheral nerve injury also induces cell division of nerve-associated glia. For this experiment, we raised ETI larvae following nerve crush on medium containing BrdU and dissected them 24 hrs later. Uninjured nerves exhibited very few BrdU-positive glia nuclei, while injured nerves exhibited extensive BrdU incorporation in Repo positive nuclei (FIG. 9A). To distinguish whether glia adjacent to the injury site were the source of the proliferating glia or if they migrated from a more distant location, we dissected pinched larvae in insect culture medium 24 hrs after the nerve crush, pulse labeled with EdU for two hours, and then fixed the larvae immediately for imaging. The results (FIG. 9B-E) indicate that the vast majority of proliferating nuclei are located immediately adjacent to the injury site on peripheral nerves (FIG. 9B-E), demonstrating that glial proliferation occurs locally at the pinch site.

Peripheral nerves contain glia that wrap individual axons (wrapping glia) and those that ensheath the nerve bundle as a whole sending projections between wrapped axons, (sub-perineurial glia or SPGs). To determine which subgroup of peripheral glia undergoes injury-induced proliferation, we performed the EdU pulse label experiment in standard larvae expressing the fluorescent nuclear marker, Red-Stinger, under the control of subtype-specific Gal4-drivers. This experiment revealed that DNA replication occurred in both wrapping glia (nrv2-Gal4 expressing) and sub-perineurial glia (moody-Gal4 or glio-Gal4 expressing) following nerve injury (FIG. 9B-E), but was most prominent in SPGs (FIGS. 9B and 9C).

Example 11

Degeneration and Clearance of Injured Sensory Axons and Synapses

In both *Drosophila* and vertebrates, after a nerve is severed axon segments distal to the cell body undergo rapid Wallerian degeneration (Lunn et al., 1989; MacDonald et al., 2006; Ayaz et al., 2008). However, little is known about degeneration of central synapses following injury to peripheral nerves in *Drosophila*. We characterized degeneration and clearance of central synapses in ETI larvae following sensory axon injury using a ppk::GFP fusion construct to observe single sensory axons. The ppk-promoter drives GFP expression in three class IV dendritic arborization neurons per hemi-segment (Grueber et al., 2002), marking three afferent axons per segmental nerve (FIG. 10A) that terminate in a lattice shaped synaptic pattern within the nociceptive neuropil of the ventral nerve cord (VNC) (FIG. 10B).

Figures 10A, 10B:
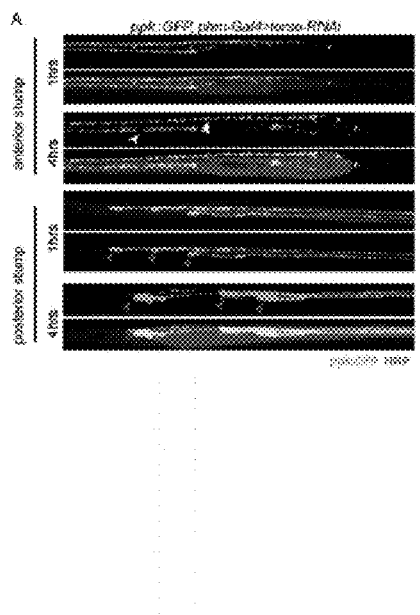
FIG. 10 Degeneration and clearance of sensory neuron axons and synapses following injury. (A) Rapid fragmentation of sensory neuron axons (white arrowheads) in anterior stumps of severed nerves, and formation of retraction bulbs in posterior stumps (red arrowhead). Confocal stacks of anterior and posterior stumps stained for GFP (green) and HRP (red) 1 and 4 hrs after injury. (B) Time course of post-injury fragmentation and clearance of sensory neuron axons (white arrowheads) and synapses (arrows). Clearance is complete by 24 hrs after injury. Confocal stacks showing the VNC and peripheral nerves of injured larvae stained for GFP (green) and HRP (red). Dotted lines indicate the position of the nerve injury relative to the segmental distribution of sensory synapses in the VNC; nerves innervating segments posterior to the dotted line were injured by pinch whereas nerves innervating segments anterior to the dotted line were spared. Insets show magnified views of the axonal projections and synaptic terminals in the areas delineated by white boxes.

One hour after nerve crush, ppk::GFP-expressing anterior axon segments (distal to sensory neuron cell bodies) were clearly disconnected from the corresponding posterior axon segments, which had retracted to form nascent retraction bulbs (FIG. 10A). Three hours later, posterior retraction bulbs had increased in size, while anterior segments of ppk-expressing axons were all fragmenting into the beaded pattern characteristic of Wallerian degeneration (FIG. 10A). Similarly, the distalmost regions of injured ppk-expressing axons immediately outside the neuropil underwent beading and degeneration within 4 hrs after nerve crush (FIG. 10B). These data indicate that sensory neuron degeneration occurs simultaneously throughout all regions of the distal axon segment and confirm the rapid induction of Wallerian degeneration in ETI larvae.

Within the neuropil, the axons and synaptic terminals of injured ppk-expressing neurons were still morphologically indistinguishable from their uninjured counterparts in more anterior segments two hours after injury (FIG. 10B). By four hours after injury, axonal beading was clearly visible in injured axons but synaptic size and morphology still appeared unchanged (FIG. 10B). At eight hours after injury, fragmentation there was substantial clearance of fragmented axonal material and synapses exhibited significant degeneration as well. By twelve hours, axons were cleared entirely and by 24 hours after injury, all GFP positive axonal and synaptic debris in the neuropil had been removed as well. These data demonstrate that injury to larval sensory axons results in rapid degeneration and clearance of severed axons that progresses distally over the course of 24 hrs until synapses also undergo degeneration and clearance.

Figure 11A:
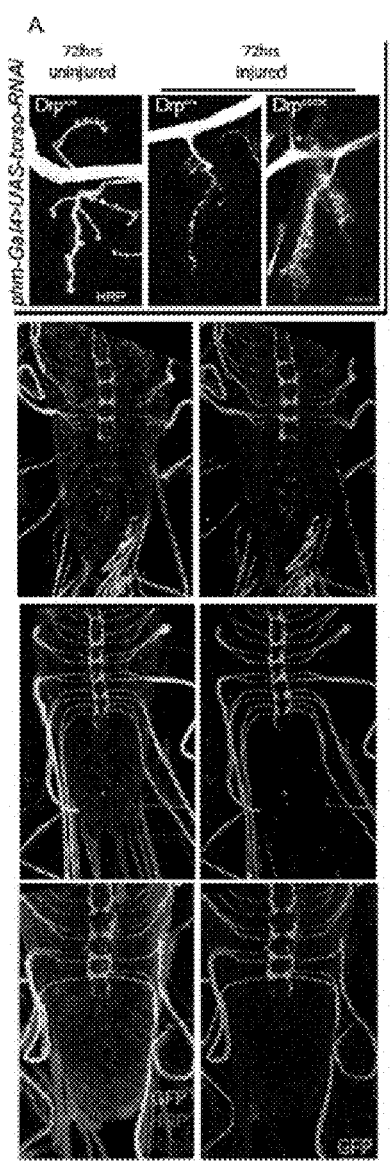
FIG. 11 draper is required for efficient clearance of fragmented NMJs and sensory neuron axonal and synaptic debris following nerve injury. (A) Synaptic debris accumulates at NMJ4 following nerve injury in draper mutant larvae compared with uninjured controls. Confocal stacks showing NMJ4 from standard (draper$^+$) ETI larvae (left) and draper mutant ETI larvae (right two panels) 72 hrs after injury. (B) Debris from sensory axons (white arrowheads) and synaptic terminals (yellow arrow head) following nerve injury persists in the VNC of draper mutant ETI larvae (three right columns) compared with its rapid disappearance in draper$^+$ ETI larvae (left two columns) Confocal stacks of VNCs labeled with antibodies against GFP (green), HRP (Red), and Repo (blue) at the indicated times following injury. White arrows in right columns indicate ppk::GFP-expressing axons in uninjured nerves anterior to the pinch site. Rightmost column shows magnified views of the axonal projections and synaptic terminals within the delineated area in the column just to the left.

Neuronal debris resulting from apoptosis during development or acute injury at adult stages in *Drosophila*, is cleared by glial phagocytic activity and dependent on the cell-corpse-engulfment receptor, draper, (Auld et al., 1995; Ito et al., 1995; Sonnenfeld and Jacobs, 1995; Freeman et al., 2003; MacDonald et al., 2006). To examine whether draper is required for the rapid clearance of sensory neuron debris following injury, of larval neurons, we tested whether loss of draper alters the time course and morphology of NMJ degeneration after nerve crush. As we found previously (FIG. 7B), 72 hrs after nerve crush, NMJs were small, spindly, and fragmented (FIG. 11A). NMJs of injured motor axons in ETI larvae lacking draper function were similarly fragmented, however large amounts of neuronal debris were present in the vicinity of the NMJ, even in regions of muscle where boutons or beaded NMJ fragments were no longer detectable (FIG. 11A).

Figure 11B:
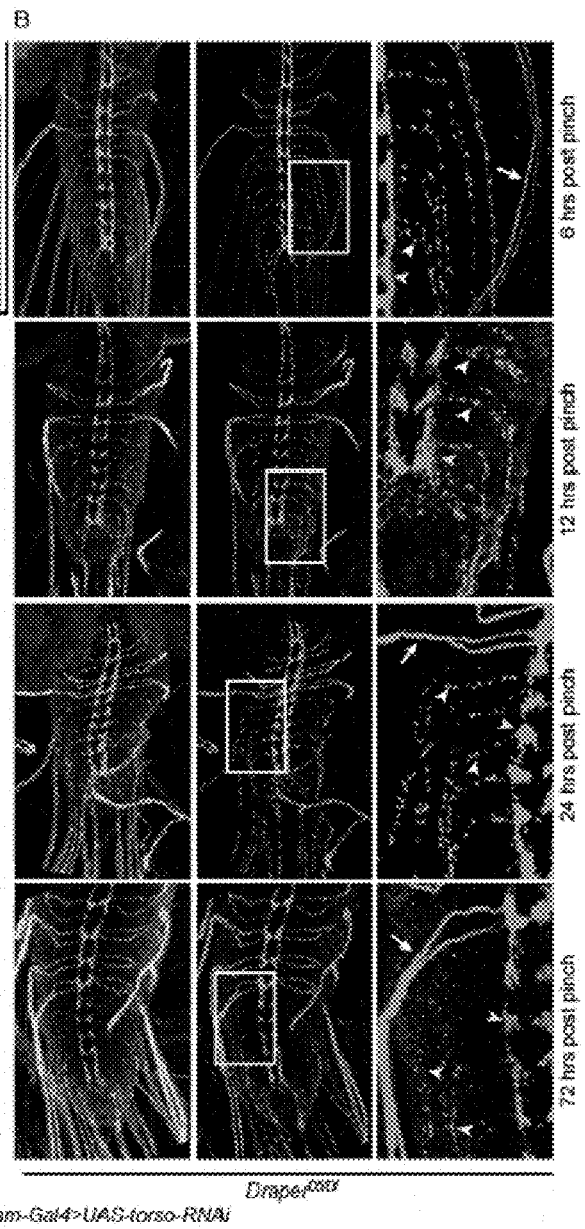

We also examined the role of draper in clearance of injured ppk-expressing sensory neurons and synapses. Loss of draper had no effect on the timing of axon fragmentation: 6hrs after injury, labeled sensory axons outside the VNC were already heavily beaded (FIG. 11B). However, whereas axonal and synaptic debris were completely cleared 12-24 hrs after injury in control larvae (FIG. 11B), in draper$^5$/Df larvae, axonal and synaptic debris persisted well beyond 48 hrs; measurable clearance of fragmented axons and synapses was not evident until 72 hrs after injury. Although diminished at this time point, sensory axonal debris was still present in draper mutants, and the signal intensity of labeled synaptic remnants was reduced by only ~50% compared with 6 hrs after injury (FIG. 11B). These findings demonstrate that draper function is required for efficient post-injury clearance of degenerating axonal and synaptic material both at the periphery and in the central nervous system.

Example 12

Regrowth of Sensory Axons Following Injury

The expanded larval period prior to metamorphosis in ETI larvae provides a unique opportunity to investigate whether and to what extent severed larval axons can regrow if allowed sufficient time to do so. To be able to follow precisely the regrowth of individual axons, we again focused on the ppk-GFP-expressing sensory axons and assessed axonal sprouting in the proximal stump at different timepoints following nerve crush. We observed the earliest evidence of sprouting 12 hours after injury, although growth was detectable at that time only in a small minority of retraction bulbs (FIG. 12A). Over time, the extent of linear regrowth increased, as did the frequency of proximal retraction bulbs that exhibited sprouting. By 24 hours after injury, we observed up to 70 μm of linear axonal growth that extended from the proximal stump into the injury site (FIG. 12A). By 72 hrs-120 hrs after injury we regularly observed linear growth of ~400 μm that extended across the injury site and invaded the distal stump of the injured nerve (FIG. 12A). At these late time points, we also observed regenerating axons that completely traversed the axotomy site and reentered the VNC. Upon reaching the VNC the regrowing axons exhibited undirected growth, invading inappropriate dorsal regions of the VNC cortex, and forming disordered patterns of branching outside of the sensory neuropil (supplemental, or data not shown). Thus, the severed axons exhibit the capacity for extensive regrowth over time, but apparently lack or cannot sense the guidance cues required to find their synaptic targets.

In vertebrates distal axon fragmentation is required for efficient axon regeneration (Perry and Brown, 1992). However, whether efficient clearance of debris is also required for regrowth is unknown. To explore this question, we measured sprouting from injured ppk-expressing sensory axons at 24 and 96 hrs following nerve crush, and calculated the average linear outgrowth in draper mutants compared with controls. Surprisingly, in draper null ETI larvae there was no significant difference in extent of linear outgrowth at 96 hrs after injury (FIG. 12B), nor was there a decrease in the frequency of regenerating axons that crossed the injury site (151 μm-300 μm) (FIG. 12D).

In the adult CNS, Draper becomes localized to membranes of glia that invade the region of neuronal fragmentation (MacDonald et al., 2006). Thus, we wondered whether draper function in glial cells might play a role in an early step required for initiating axonal sprouting. Consistent with this notion, immunostaining revealed that Draper was present at very low levels in uninjured nerve bundles but was readily detectable in stumps of injured nerves (FIG. 12B) 24 hrs after nerve crush, with a 2.5-fold increase in staining intensity compared with uninjured nerves. Draper appears to be localized at regions of the stump where HRP staining is low (FIG. 12B) suggesting that it is most likely associated with the membrane of glial cells that are recruited to the site of peripheral nerve injury. Moreover, 24 hrs after injury, regrowth of injured axons exhibited a significant decrease in average outgrowth length in draper mutants (FIG. 12C). This decrease was concomitant with a threefold increase in the frequency of retraction bulbs that show minimal or no axonal sprouting (10% in draper mutants vs. 30% in controls) at 24 hrs (FIG. 12D). Together, these data indicate that Draper-dependent clearance of axonal debris from injured nerve stumps is not required for axonal growth across the injury site and into the distal nerve bundle. Instead our findings suggest that Draper is recruited to sites of nerve injury and plays an important role in promoting the initiation of axonal sprouting from retraction bulbs following axotomy

REFERENCES

Auld V J, Fetter R D, Broadie K, Goodman C S (1995) Gliotactin, a novel transmembrane protein on peripheral glia, is required to form the blood-nerve barrier in *Drosophila*. Cell 81:757-767.

Ayaz D, Leyssen M, Koch M, Yan J, Srahna M, Sheeba V, Fogle K J, Holmes T C, Hassan B A (2008) Axonal injury and regeneration in the adult brain of *Drosophila*. J Neurosci 28:6010-6021.

Daniels R W, Collins C A, Gelfand M V, Dant J, Brooks E S, Krantz D E, DiAntonio A (2004) Increased expression of the *Drosophila* vesicular glutamate transporter leads to excess glutamate release and a compensatory decrease in quantal content. J Neurosci 24:10466-10474.

Freeman M R, Delrow J, Kim J, Johnson E, Doe C Q (2003) Unwrapping glial biology: Gcm target genes regulating glial development, diversification, and function. Neuron 38:567-580.

Grueber W B, Jan L Y, Jan Y N (2002) Tiling of the *Drosophila* epidermis by multidendritic sensory neurons. Development 129:2867-2878.

Ito K, Urban J, Technau G (1995) Distribution, classification, and development of *Drosophila* glial cells in the late embryonic and early larval ventral nerve cord. Development Genes and Evolution 204:284-307.

Kato K, Awasaki T, Ito K (2009) Neuronal programmed cell death induces glial cell division in the adult *Drosophila* brain. Development 136:51-59.

Kato K, Forero M G, Fenton J C, Hidalgo A (2011) The glial regenerative response to central nervous system injury is enabled by pros-notch and pros-NFkappaB feedback. PLoS Biol 9:e1001133.

Lunn E R, Perry V H, Brown M C, Rosen H, Gordon S (1989) Absence of Wallerian Degeneration does not Hinder Regeneration in Peripheral Nerve. Eur J Neurosci 1:27-33.

MacDonald J M, Beach M G, Porpiglia E, Sheehan A E, Watts R J, Freeman M R (2006) The *Drosophila* cell corpse engulfment receptor Draper mediates glial clearance of severed axons. Neuron 50:869-881.

Miller D L, Ballard S L, Ganetzky B (2012) Analysis of synaptic growth and function in *Drosophila* with an extended larval stage. J Neurosci In Press.

Perry V H, Brown M C (1992) Role of macrophages in peripheral nerve degeneration and repair. Bioessays 14:401-406.

Sonnenfeld M J, Jacobs J R (1995) Macrophages and glia participate in the removal of apoptotic neurons from the *Drosophila* embryonic nervous system. J Comp Neurol 359:644-652.

Xiong X, Collins C A (2012) A conditioning lesion protects axons from degeneration via the Wallenda/DLK MAP kinase signaling cascade. J Neurosci 32:610-615.

Xiong X, Wang X, Ewanek R, Bhat P, Diantonio A, Collins C A (2010) Protein turnover of the Wallenda/DLK kinase regulates a retrograde response to axonal injury. J Cell Biol 191:211-223.

Zito K, Fetter R D, Goodman C S, Isacoff E Y (1997) Synaptic clustering of Fascilin II and Shaker: essential targeting sequences and role of Dlg. Neuron 19:1007-1016.

Example 13

A Stathmin Mutation Induces Long Term Neuromuscular Degeneration in ETI Larva Here we test whether the extended third instar (ETI) system can be utilized to model neurodegenerative phenotypes at the single synapse level. As a first step we focused on gene that is required for NMJ stability during normal larval development (1) and is associated with neurodegenerative phenotypes in vertebrates (2, 3), Stathmin (stai). NMJ destabilization in stai mutant larvae is evidenced by the appearance of post-synaptic densities that lack properly apposed presynaptic structures, called footprints. It is not clear whether footprints are a transient feature of destabilized NMJs in stai mutants, or whether footprints accumulate with time resulting in permanent loss of presynaptic structures. To test whether loss of stathmin function causes permanent rather than dynamic retractions of the presynapse, we placed a *Drosophila* stai mutation (stai B200) into the ETI background and characterized NMJ structure during the extended third instar. For this experiment we utilized smoxETI, a variant of the ETI system that prolongs the life span of third instar larvae to up to 600 hrs after egg lay (see Methods), to provide maximum time for stai defects to take effect. Our preliminary data suggest that loss of stathmin leads to: (1) a time-dependent accumulation of apposition defects at larval NMJs with most boutons exhibiting loss of presynaptic machinery by 504 hrs AEL; and (2) whole-sale retraction of about 20% of NMJs by 504 hrs AEL. Uncovering these novel neurodegenerative phenotypes mutant stathmin was crucially facilitated by the smoxETI system, underscoring its promise as an experimental model in which to probe time-dependent neurodegeneration at the single synapse level.

Methods

Fly Stocks w1118 was used as a wild-type control for genetic background, and experiments were performed in a w1118 background. phm-Gal4 (5) and UAS-smox RNAi (6). The following stocks were obtained from the Bloomington Stock Center: stai$^{B200}$ (stai loss of function caused by a P-element insertion in the stathmin gene).

Developmental Timing of Larvae and Immunohistochemistry

As described previously (4)

Imaging and Quantification and Statistical Analyses

As described previously (4)

Figure 13:
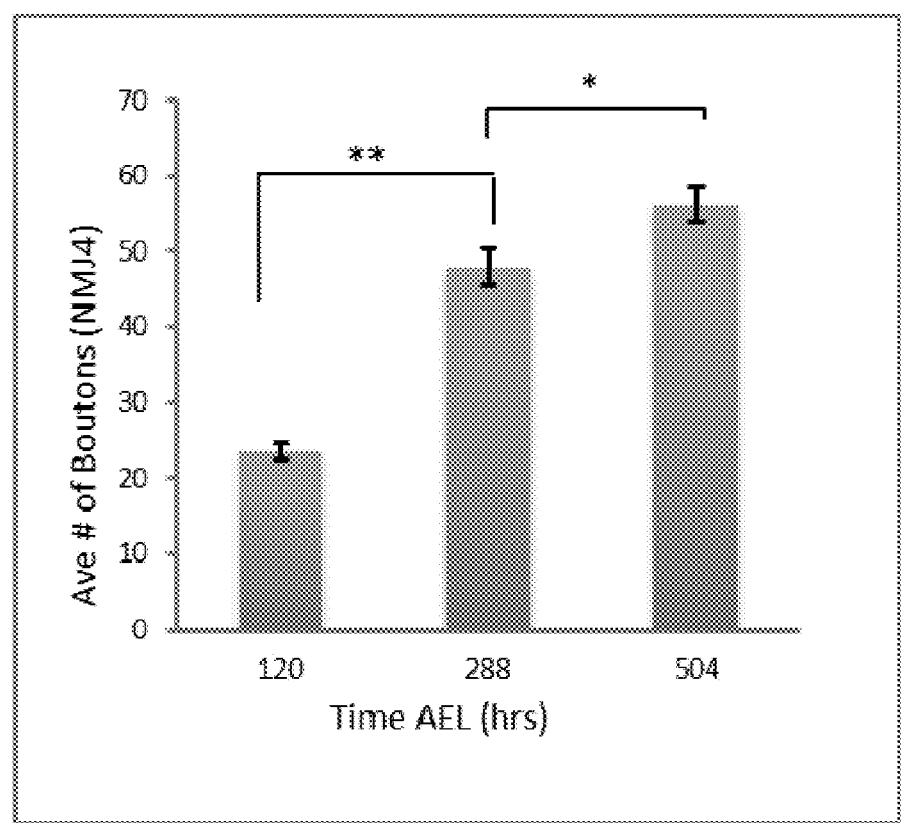
FIG. 13 Characterization of bouton number at NMJ4 of smox ETI larvae. The average verage bouton number at NMJ4 continues to increase during the prolonged third instar of smoxETI larvae. $*p<0.01$, $**p<0.001$.

Extending the life span of *Drosophila* larvae to 300 hrs after egg lay leads to continued growth of the larval NMJ without loss of structural integrity(4). To assess the growth pattern of NMJs in the longer lived smoxETI (larval stage persist for an additional 300 hrs), we performed a time-course analysis of bouton number at NMJ4 in smoxETI larvae from 120 to 504 hrs after egg lay (AEL). We found that, similar to larvae expressing torso RNAi in the prothoracic gland (phm>torsoRNAi), NMJ4 added boutons throughout the smoxETI period, growing from an average of 24 boutons at 120 hrs AEL, to 56 boutons at 504 hrs (FIG. 13). Staining for proteins of the pre and post-synaptic machinery as well as electrophysiological analysis reveals no accumulation of abnormalities in NMJ structure or function in smoxETI (data not shown).

Figure 14A:
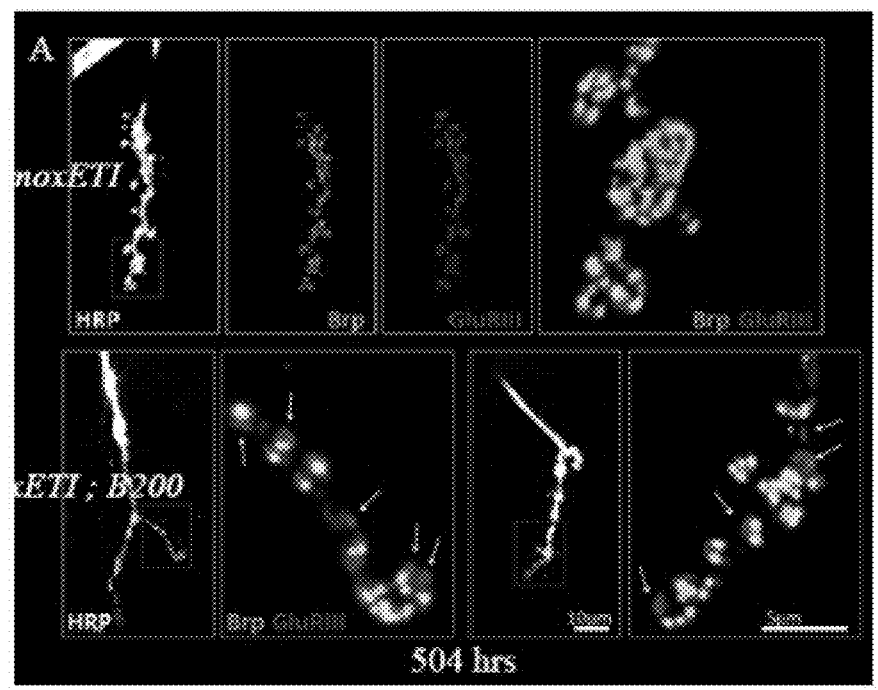
FIG. 14 Time-dependent accumulation of apposition defects in smox ETI; B200/B200 larvae (A) Loss of stathmin function in smoxETI larvae leads to the appearance of post-synaptic receptor fields (GluRIII, red) that lack properly apposed presynaptic release machinery (Brp, green). (B) Apposition defects accumulate with time in stathmin mutant (B200/B200) smoxETI larve, but not in smoxETI larvae. $*p<0.01$, $**p<0.001$, and n.s.=not statistically significant FIG. 15 Time-dependent retraction of NMJs in smox ETI; b200/b200 larvae (A) Presence and absence of neuromuscular junctions on muscle 4 of equivalent segments at 504 hours AEL. Retractions in mutant larvae show a clear defasciculation, but no boutons, little elaborations, and complete absence of Brp (red) or GluRIII staining. (B) Quantification of NMJ retraction frequency with time.
Figure 14B:
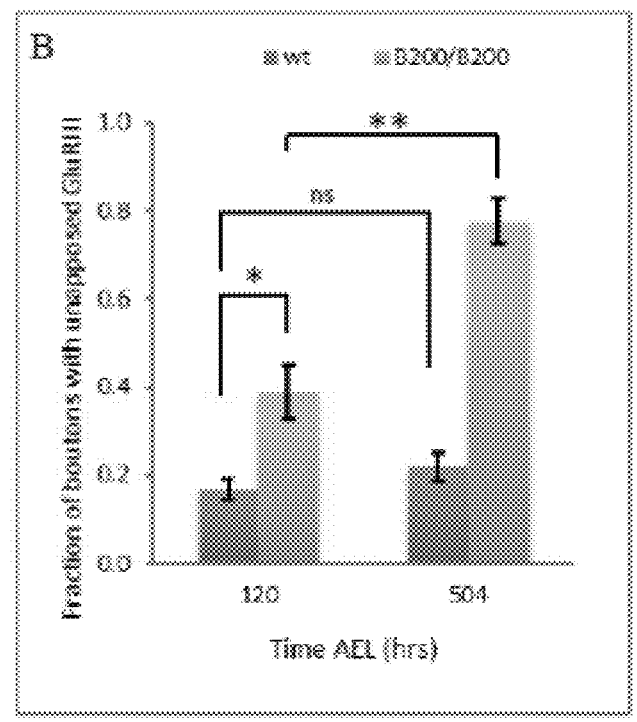

To test whether loss of stathmin causes time-dependent accumulation of synaptic defects we introduced a loss of function mutation (staib200) into the smoxETI background and counted the frequency of boutons that exhibited apposition defects. We labeled pre and post synaptic machinery components by staining for the active-zone glutamate release machinery protein Bruchpilot (Brp) and the post-synaptic glutamate receptor GluRI1I. In smoxETI larvae that are wild-type for stathmin approximately 17% of NMJ4 boutons show apposition defects at 120 hrs AEL (FIG. 14B). This baseline remains unchanged throughout the extended third instar (FIG. 2, A,B). NMJ4 in smoxETI larvae lacking functional stathmin exhibit clear apposition defects ~40% of boutons by 120 hrs AEL, and the fraction of effected boutons increases to nearly 80% by 504 hrs AEL (FIGS. 14A and B).

Figure 15A:
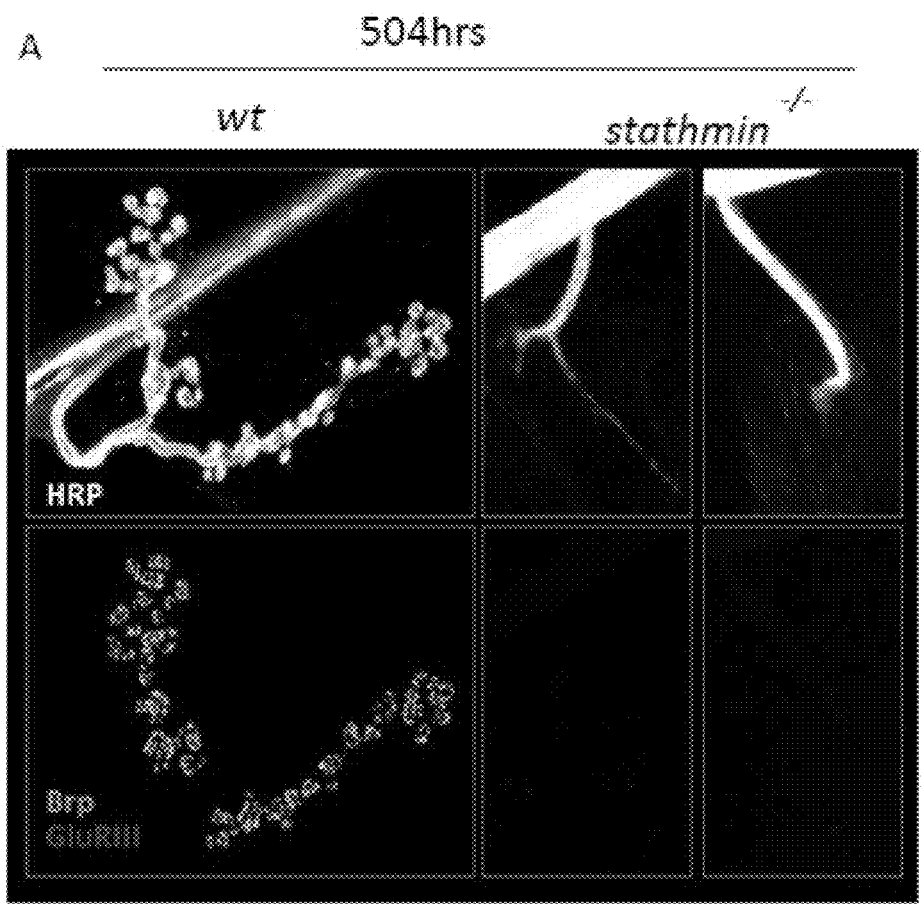
Figure 15B:
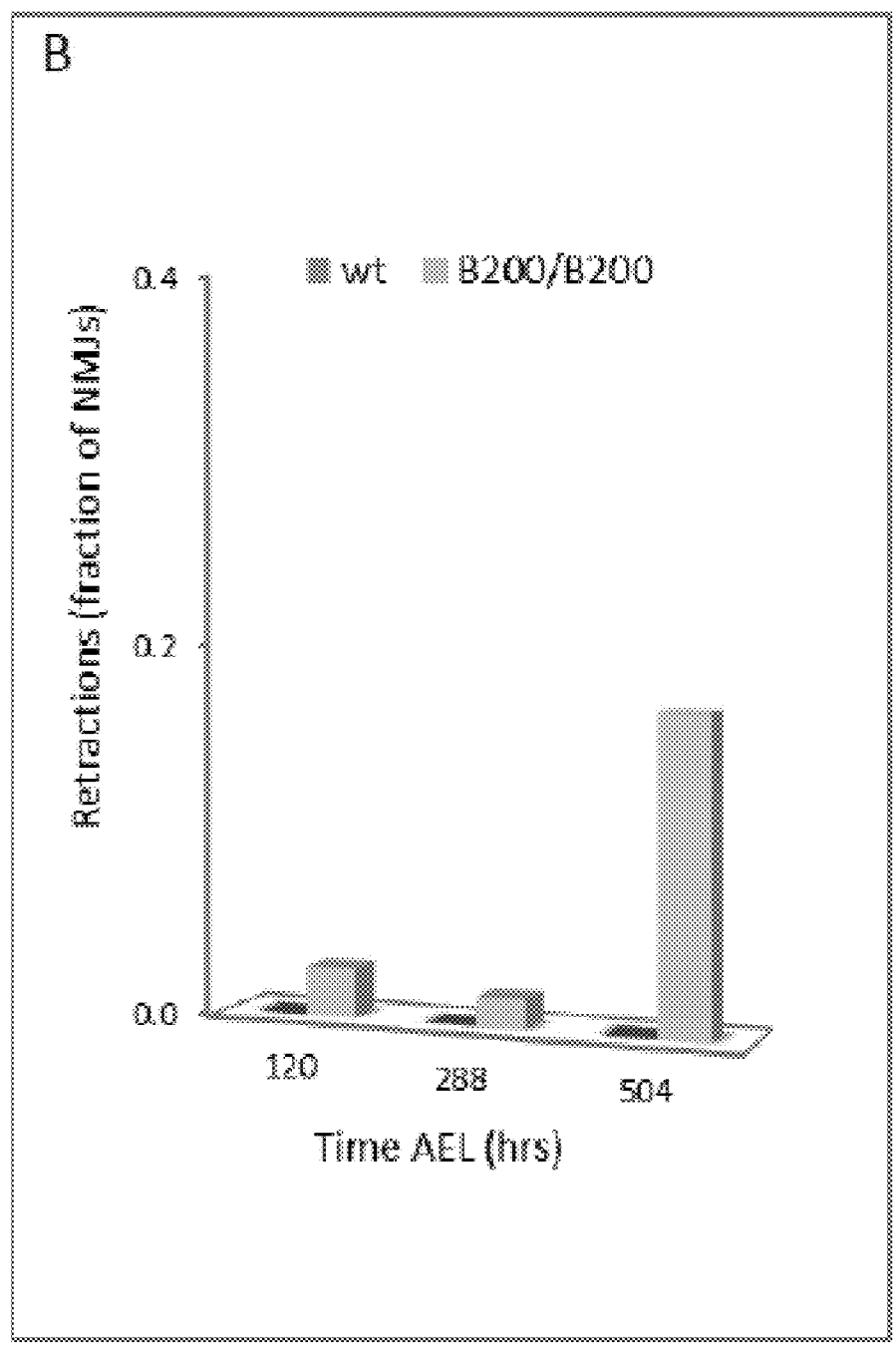

Next, we asked whether we could detect any wholesale loss of presynaptic structures, or NMJ retractions. We defined a retracted NMJ as a motor axon defasciculation that evidenced no presynaptic boutons and a complete absence of pre and post-synaptic proteins. Throughout the smoxETI life-span we could detect no retracted NMJs in larvae with wild type stathmin (FIGS. 15A and B). In smoxETI larvae that are homozygous for the stai b200 allele NMJ retractions accumulate in a time-dependent fashion. At 120 and 288 hrs AEL, less than 5% of NMJ's are retracted, however by 504 hrs AEL ~20% of muscle 4 fibers are completely denervated (FIGS. 15A and B).

Together these data shed new light on the requirement for stathmin in NMJ maintenance. We show that loss of stathmin leads to progressive loss of synapse integrity and ultimately results in complete denervation. The synaptic defects, both loss of apposition and NMJ retraction, are most pronounced in the posterior segments of the larva, and are expressed in a gradient that increases from anterior to posterior segments (data not shown). This finding correlates with an onset of paralysis in posterior segments at ~300 hrs AEL, which, with increasing time, affects progressively more anterior segments. In sum, these results establish the smoxETi system as a powerful model in which to probe mechanisms of synapse degeneration, identify new genes and pathways that are required for synapse stability, and in which to screen for drugs with potential therapeutic application to neurodegenerative disorders.

REFERENCES

1. E. R. Graf, H. M. Heerssen, C. M. Wright, G. W. Davis, A. DiAntonio, *J Neurosci* 31, 15026 (Oct. 19, 2011).
2. H. L. Wen et al., *Hum Mol Genet* 19, 1766 (May 1, 2010).
3. H. L. Wen, C. H. Ting, H. C. Liu, H. Li, S. Lin-Chao, *Neurobiol Dis* 52, 94 (April 2013).
4. D. L. Miller, S. L. Ballard, B. Ganetzky, *J Neurosci* 32, 13776 (Oct. 3, 2012).
5. K. F. Rewitz, N. Yamanaka, L. I. Gilbert, M. B. O'Connor, *Science* 326, 1403 (Dec. 4, 2009).
6. Y. Y. Gibbens, J. T. Warren, L. I. Gilbert, M. B. O'Connor, *Development* 138, 2693 (July 2011).

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

What is claimed is:

1. A method for identifying an agent that modulates motor or sensory neuron axon regeneration in an extended third instar (ETI) *Drosophila* larva, comprising:
   (i) contacting with a test agent an ETI *Drosophila* larva comprising a structural or functional disruption of one or more motor or sensory neuron axons;
   (ii) assessing motor or sensory neuron axon regeneration in the disrupted motor or sensory neuron axons by assessing one or more of growth of the disrupted motor or sensory neuron axons, neuromuscular junction formation, glial activation, motor or sensory neuron survival, or neuromuscular junction loss in the contacted ETI Drosophila larva, and
   (iii) identifying the test agent as an agent that modulates motor or sensory neuron axon regeneration if a result of the assessment of step (ii) in the presence of test agent differs from the result of the assessment in the absence of the test agent.

2. The method of claim 1, wherein the ETI *Drosophila* larva comprises a genetic modification that reduces expression of torso in the prothoracic gland relative to expression of torso in the prothoracic gland of a *Drosophila* that does not comprise the genetic modification.

3. The method of claim 2, wherein the genetic modification comprises a transgene to express torso RNAi.

4. The method of claim 3, wherein the torso RNAi is expressed selectively in the prothoracic gland.

5. The method of claim 4, wherein the genetic modification comprises a phm-Gal4 transgene and a UAS-torso RNAi transgene.

6. The method of claim 1, wherein the ETI *Drosophila* larva comprises a genetic modification to reduce expression of Smad2 in the prothoracic gland.

7. The method of claim 6, wherein the genetic modification comprises a phm-Gal4 transgene and a UAS-Smad2 RNAi transgene.

8. The method of claim 1, wherein the ETI *Drosophila* larva comprises a phm-Gal4 transgene and a UAS promoter driving expression of an RNAi against ras85D RNAi, or ERK RNAi.

9. The method of claim 1, wherein the contacting step is performed at least about 144 hours after the egg for the ETI *Drosophila* larva is laid.

10. The method of claim 1, wherein the contacted ETI *Drosophila* larva comprises a nerve pinch injury to the one or more motor neurons.

11. The method of claim 1, wherein the contacted ETI *Drosophila* larva comprises a genetic modification that induces the structural or functional disruption of the one or more motor neurons.

12. The method of claim 11, wherein the genetic modification results in expression of at least one heterologous polypeptide associated with a neurodegenerative disease.

13. The method of claim 12, wherein the at least one heterologous polypeptide comprises a hAPP, hAbeta$^{1-42}$, a hTau, a hsynuclein, hhuntingtin, a hTDP-43, a hSOD, hLRRK2, a hGSK3β, or any combination thereof.

* * * * *

UNITED STATES PATENT AND TRADEMARK OFFICE
CERTIFICATE OF CORRECTION

| | | |
|---|---|---|
| PATENT NO. | : 9,568,468 B2 | Page 1 of 1 |
| APPLICATION NO. | : 14/212999 | |
| DATED | : February 14, 2017 | |
| INVENTOR(S) | : Barry Ganetzky, Daniel L. Miller and Shannon L. Ballard | |

It is certified that error appears in the above-identified patent and that said Letters Patent is hereby corrected as shown below:

In the Specification

Column 19, Line 51 - "2/NMJ4)" should be --(< 2/NMJ4)--.

Column 20, Line 44 - "with" should be --wit--.

Column 20, Line 47 - "with" should be --wit--.

Column 20, Line 49 - "with" should be --wit--.

Column 20, Line 54 - "with" should be --wit--.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*